(12) United States Patent
Kawai et al.

(10) Patent No.: US 8,038,689 B2
(45) Date of Patent: Oct. 18, 2011

(54) INTRACOELOMIC SUTURING AND LIGATING METHOD

(75) Inventors: Junko Kawai, Shibuya-ku (JP); Shigeru Omori, Ashigarakami-gun (JP); Shuichi Uenohara, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 645 days.

(21) Appl. No.: 12/076,771

(22) Filed: Mar. 21, 2008

(65) Prior Publication Data

US 2009/0240263 A1    Sep. 24, 2009

(51) Int. Cl.
*A61B 17/04* (2006.01)
*A61B 17/12* (2006.01)

(52) U.S. Cl. ......... 606/144; 606/139; 606/147; 606/148

(58) Field of Classification Search .................. 606/139, 606/1, 140, 144–150, 205–209, 222–227; 128/898; 600/29, 30, 104, 135
See application file for complete search history.

(56) References Cited

U.S. PATENT DOCUMENTS

| | | | | |
|---|---|---|---|---|
| 5,047,039 | A * | 9/1991 | Avant et al. | 606/148 |
| 5,830,220 | A * | 11/1998 | Wan et al. | 606/139 |
| 5,951,575 | A * | 9/1999 | Bolduc et al. | 606/144 |
| 6,468,265 | B1 * | 10/2002 | Evans et al. | 606/1 |
| 6,889,116 | B2 * | 5/2005 | Jinno | 700/245 |
| 6,921,408 | B2 * | 7/2005 | Sauer | 606/144 |
| 7,419,080 | B2 * | 9/2008 | Smith et al. | 227/175.1 |
| 7,464,847 | B2 * | 12/2008 | Viola et al. | 227/175.2 |
| 2008/0091072 | A1 * | 4/2008 | Omori et al. | 600/131 |

FOREIGN PATENT DOCUMENTS

JP    2002-102248 A    4/2002

OTHER PUBLICATIONS

Ahlering et al., Robotic Radical Prostatectomy: A Technique to Reduce pT2 Positive Margins, Jan. 2005, Urology by Elsevier Science Inc., vol. 64, Issue 6, pp. 1224-1228.*
Ahlering et al., Robotic Radical Prostatectomy: A Technique to Reduce pT2 Positive Margins, Jan. 2005, Urology by Elsevier Science Inc., vol. 64, Issue 6, pp. 1224-1228 available at http://www.sciencedirect.com/science/article/pii/S0090429504009604.*
Tewari et al., Technique of da Vinci Robot-Assisted Anatomic Radical Prostatectomy, Oct. 2002, Urology by Elsevier Science Inc., vol. 60, Issue 4, pp. 569-572.*
Tewari et al., Technique of da Vinci Robot-Assisted Anatomic Radical Prostatectomy, Oct. 2002, Urology by Elsevier Science Inc., vol. 60, Issue 4, pp. 569-572 available at http://www.sciencedirect.com/science/article/pii/S0090429502018526.*

* cited by examiner

*Primary Examiner* — Corrine M McDermott
*Assistant Examiner* — Todd J Scherbel
(74) *Attorney, Agent, or Firm* — Buchanan Ingersoll & Rooney PC

(57) ABSTRACT

A manipulator includes a composite input unit that is manually operable by the fingers, a connector shaft extending from an operating unit, and a working unit mounted on the distal end of the connector shaft. The working unit comprises a rolling mechanism, a tilting mechanism, and an opening and closing mechanism. The composite input unit includes a shuttle ring for actuating the rolling mechanism. The manipulator also includes a gripper for gripping a curved needle. The gripper is placed near a DVC, whereupon the rolling mechanism is actuated to roll the gripper and to pierce a living body with the curved needle, until the point of the curved needle projects outside of the living body.

10 Claims, 21 Drawing Sheets

INTRACOELOMIC SUTURING AND LIGATING METHOD

BACKGROUND OF THE INVENTION

1. Field of the Invention

The present invention relates to an intracoelomic suturing and ligating method for use in performing a prostatectomy with a manipulator having an operating unit to be gripped by hand, a connector extending from the operating unit, and a working unit mounted on a distal end of the connector, which is angularly movable in response to operation of the operating unit.

2. Description of the Related Art

In endoscopic surgery (also called laparoscopic surgery), it is customary to form a plurality of incisions in the body surface of the patient, insert trocars (tubular instruments) into the respective incisions as forceps instrument passage ports, and introduce the tip ends of forceps instruments having shafts through the respective trocars and into the body cavity in order to perform a surgical operation on the affected part of the body. Working units such as a gripper for gripping living tissue, scissors, the blade of an electrosurgical knife, etc., may be mounted on the tip ends of such forceps instruments.

An endoscopic surgical operation performed with forceps instruments requires the surgeon to be trained in advance, because the working space within the body cavity is small, and the forceps instruments need to be operated using the trocars as fulcrums. Since forceps instruments, which have been used heretofore, do not have joints in the working unit on the tip end thereof, such forceps instruments have a small degree of freedom, and the working unit can be operated only on an extension of the shaft. Therefore, cases that can be handled under usual training practices for endoscopic surgery are limited to a certain range, and the surgeon must be trained and possess a considerably high level of skill in order to be able to perform endoscopic surgeries on various other cases that lie outside of this limited range.

Attempts have heretofore been made to improve conventional forceps instruments and to develop a forceps instrument having a plurality of joints in a working unit thereof (see, for example, Japanese Laid-Open Patent Publication No. 2002-102248). This developed forceps instrument, which may also be referred to as a manipulator, is free of the limitations and difficulties posed by conventional forceps instruments, can be operated with easy techniques, and can be applied to a wide variety of cases. For example, it is expected that the developed forceps instrument will be applied to techniques requiring intricate manipulative actions inside of small spaces. One example of such techniques is DVC ligation, for ligating a DVC (Dorsal Vein Complex) during a prostatectomy procedure. It has been difficult to perform DVC ligation when performing endoscopic surgeries using conventional techniques and methods.

SUMMARY OF THE INVENTION

It is an object of the present invention to provide an intracoelomic suturing and ligating method for facilitating a technique of passing a curved needle through a portion of a living body, and removing the curved needle from the surface of the living body, even at deep positions within a narrow body cavity.

According to the present invention, there is provided an intracoelomic suturing and ligating method for use in performing a prostatectomy with a manipulator having an operating unit to be gripped by hand, a connector extending from the operating unit, and a working unit mounted on the distal end of the connector, the manipulator including a rolling mechanism, a tilting mechanism, and an opening and closing mechanism, comprising the steps of a) inserting the working unit into a body cavity in a living body, b) gripping a curved needle with the opening and closing mechanism, c) tilting the opening and closing mechanism with the tilting mechanism, d) placing the opening and closing mechanism near a DVC in the body cavity, and e) actuating the rolling mechanism to angularly move the opening and closing mechanism so as to pierce the living body with the curved needle until a needle point of the curved needle projects from the living body in surrounding relation to the DVC, for thereby ligating the DVC.

With the intracoelomic suturing and ligating method, the rolling mechanism is actuated to easily perform a surgical technique of passing the curved needle through the tissue region behind the DVC and then removing the curved needle from the tissue region, even if the working unit is placed deeply inside of a small body cavity.

The steps referred to above do not need to be carried out in the order named, but may be carried out in other sequences. For example, steps b) and c) may be switched around.

The intracoelomic suturing and ligating method is particularly preferable when applied to DVC ligation performed during a prostatectomy procedure.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENT

An intracoelomic suturing and ligating method according to an embodiment of the present invention will be described below with reference to FIGS. 1 through 21C. The intracoelomic suturing and ligating method according to the embodiment of the present invention is carried out using a manipulator 10 (see FIG. 1) and is applied to endoscopic surgical operations or the like.

Figure 1:
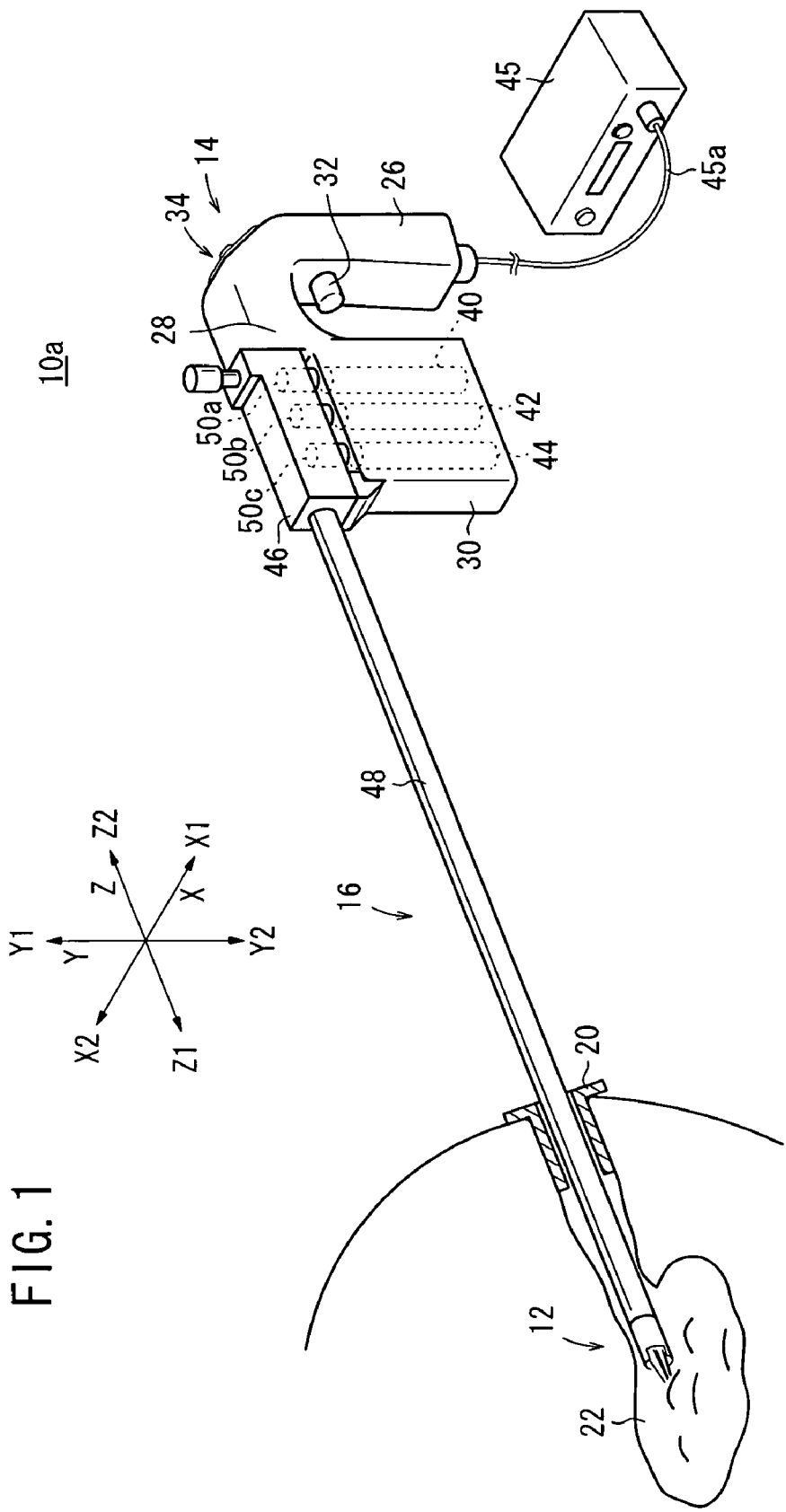
FIG. 1 is a perspective view, as seen obliquely from a front end, of a manipulator that is used to carry out an intracoelomic suturing and ligating method according to an embodiment of the present invention.

As shown in FIG. 1, the manipulator 10 has a working unit 12 on its tip end for gripping a portion of a living tissue, a curved needle, or the like. The working unit 12 is typically referred to as gripping forceps or a needle driver (needle holder).

Figure 2:
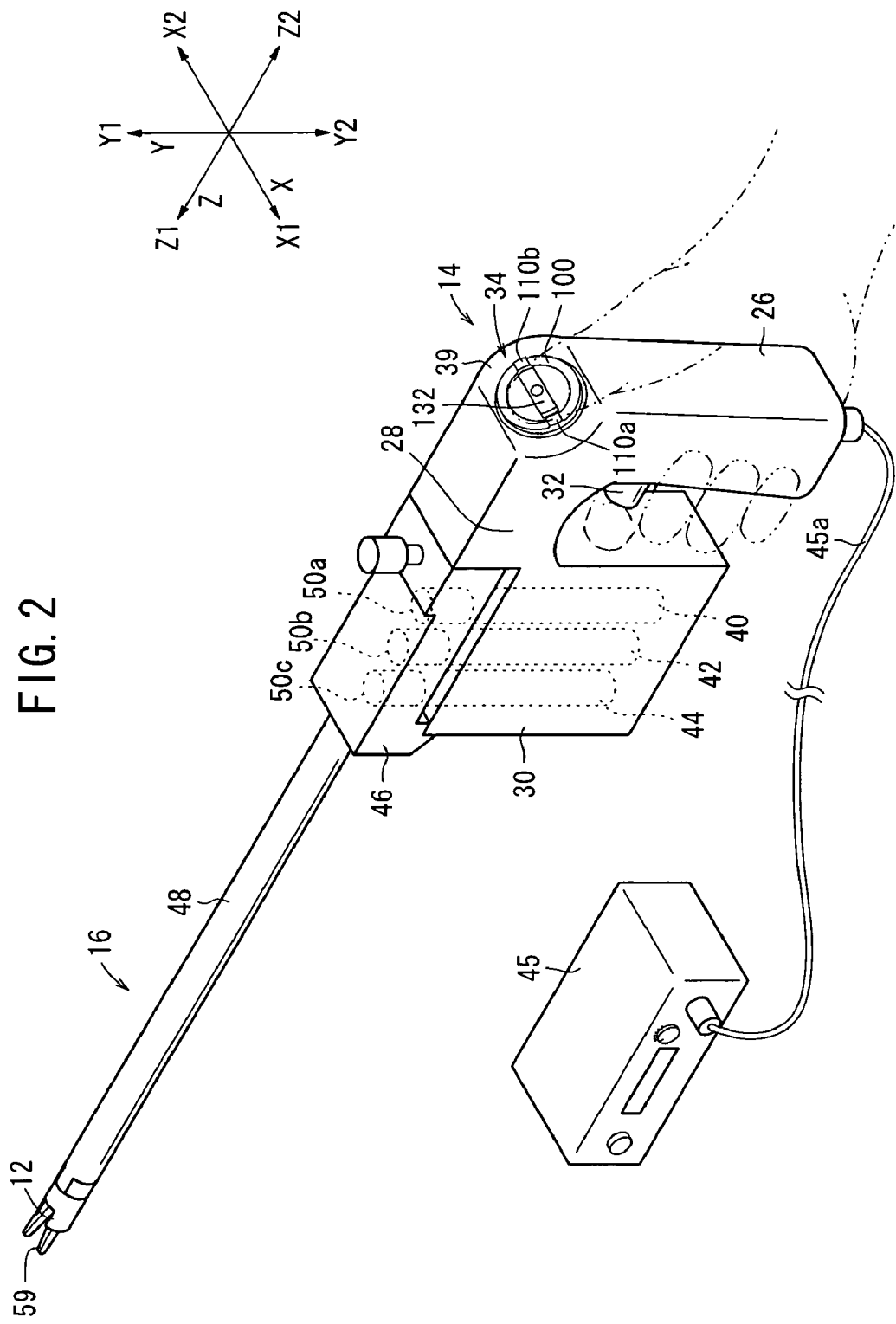
FIG. 2 is a perspective view, as seen obliquely from a rear end, of the manipulator.

As shown in FIGS. 1 and 2, the manipulator 10 comprises an operation command unit (operating unit) 14 on a proximal end thereof which is held and operated by hand, a working unit 12 on a distal end thereof for working on a living tissue, and an elongate connector 16 interconnecting the working unit 12 and the operation command unit 14. The working unit 12 and the connector 16 are of a small diameter and can be inserted into a body cavity 22 through a trocar 20 in the form of a hollow cylinder mounted in an abdominal region or the like of the patient. The working unit 12 is actuated by the operation command unit 14 to perform various techniques to grip, remove, suture, or ligate an affected part of the patient's body within the body cavity 22.

It is assumed in the following descriptions that transverse directions of the manipulator 10 are referred to as X directions, vertical directions as Y directions, and longitudinal directions of the connector 16 as Z directions. Among the X directions, the rightward direction is referred to as an X1 direction, and the leftward direction as an X2 direction. Among the Y directions, the upward direction is referred to as an Y1 direction, and the downward direction as a Y2 direction. Among the Z directions, the forward direction is referred to as a Z1 direction, and the rearward direction as a Z2 direction. Unless otherwise noted, these directions represent directions of the manipulator 10 when it is in a neutral posture. The above directional definitions are for illustrative purpose only, and the manipulator 10 can be used in any orientation, e.g., it may be used upside down.

The operation command unit 14 includes a grip handle 26 gripped by hand, a bridge 28 extending from an upper portion of the grip handle 26, and an actuator block 30 connected to a distal end of the bridge 28. The grip handle 26 may have a lower end thereof connected to a lower end of the actuator block 30.

The grip handle 26 extends in the Y2 direction from the end of the bridge 28, and is of a length that is suitable for being gripped by the hand. The grip handle 26 includes a trigger lever 32 and a composite input unit 34 serving as an input means. The trigger lever 32 is positioned slightly beneath the bridge 28 and projects slightly in the Z1 direction. The trigger lever 32 is disposed in a position where it can easily be pulled by the index finger of the hand that grips the grip handle 26.

The composite input unit 34 serves as a composite input means for applying rotational commands in both rolling directions (directions about a roll axis) and yawing directions (leftward and rightward directions about a yaw axis) to the working unit 12. The composite input unit 34 has a circular shape when viewed in front elevation (see FIG. 7), and is provided on a flat area 39 of the joint between the upper end of the grip handle 26 and the bridge 28. As can be seen from FIG. 2, the composite input unit 34 is disposed in a position where it can easily be operated by the thumb of the hand that grips the grip handle 26.

The flat area 39 has a substantially annular shape, which is larger in diameter than the composite input unit 34. When the composite input unit 34 is not operated, the user, typically a surgeon, places his or her thumb on the flat area 39, so that the user can firmly grip the grip handle 26 without touching the composite input unit 34. A line normal to the flat area 39 and the surface of the composite input unit 34 extends along a direction that lies at a substantially intermediate location between the Z2 direction and the Y1 direction. Therefore, the user can place the pad T (see FIG. 5) of the thumb naturally against the flat area 39 and on the surface of the composite input unit 34. The pad T refers to a portion of the thumb, which extends from the first joint (closest to the fingertip) to the fingertip, and which lies on the same side as the palm of the hand. Details of the composite input unit 34 shall be described later.

The actuator block 30 houses therein three motors 40, 42, 44 corresponding to respective mechanisms providing three degrees of freedom, which are incorporated in the working unit 12. The motors 40, 42, 44 are arrayed in parallel in the longitudinal direction of the connector 16. The motors 40, 42, 44 are small in size and diameter, thereby allowing the actuator block 30 to have a compact flat shape. The actuator block 30 is disposed downwardly of the end of the operation command unit 14 in the Z1 direction. The motors 40, 42, 44 can be energized to rotate the drive shafts thereof under the control of a controller 45, based on operations of the operation command unit 14.

The controller 45, which serves to control the manipulator 10 electrically, is connected by a cable 45a to a connector on the lower end of the grip handle 26.

The connector 16 includes a joint 46 joined to the actuator block 30, and a hollow connector shaft 48 extending in the Z1 direction from the joint 46. The joint 46 houses drive pulleys 50a, 50b, 50c therein, which are connected respectively to the drive shafts of the motors 40, 42, 44. Wires 52, 53, 54 (see FIG. 3) are trained respectively around the pulleys 50a, 50b, 50c and extend through a space 48a in the connector shaft 48 to the working unit 12. The wires 52, 53, 54 may be of the same type and have the same diameter.

The joint 46 can be manually operated according to a predetermined process in order to disconnect the connector 16 from the operation command unit 14 for cleaning, sterilization, maintenance, and the like. The connector 16 and the working unit 12 can be replaced with other connectors and other working units. For example, depending on the technique required for a certain surgical operation, the connector 16 may be replaced with a connector having a different length and/or the working unit 12 may be replaced with a working unit that incorporates different mechanisms therein.

Figure 3:
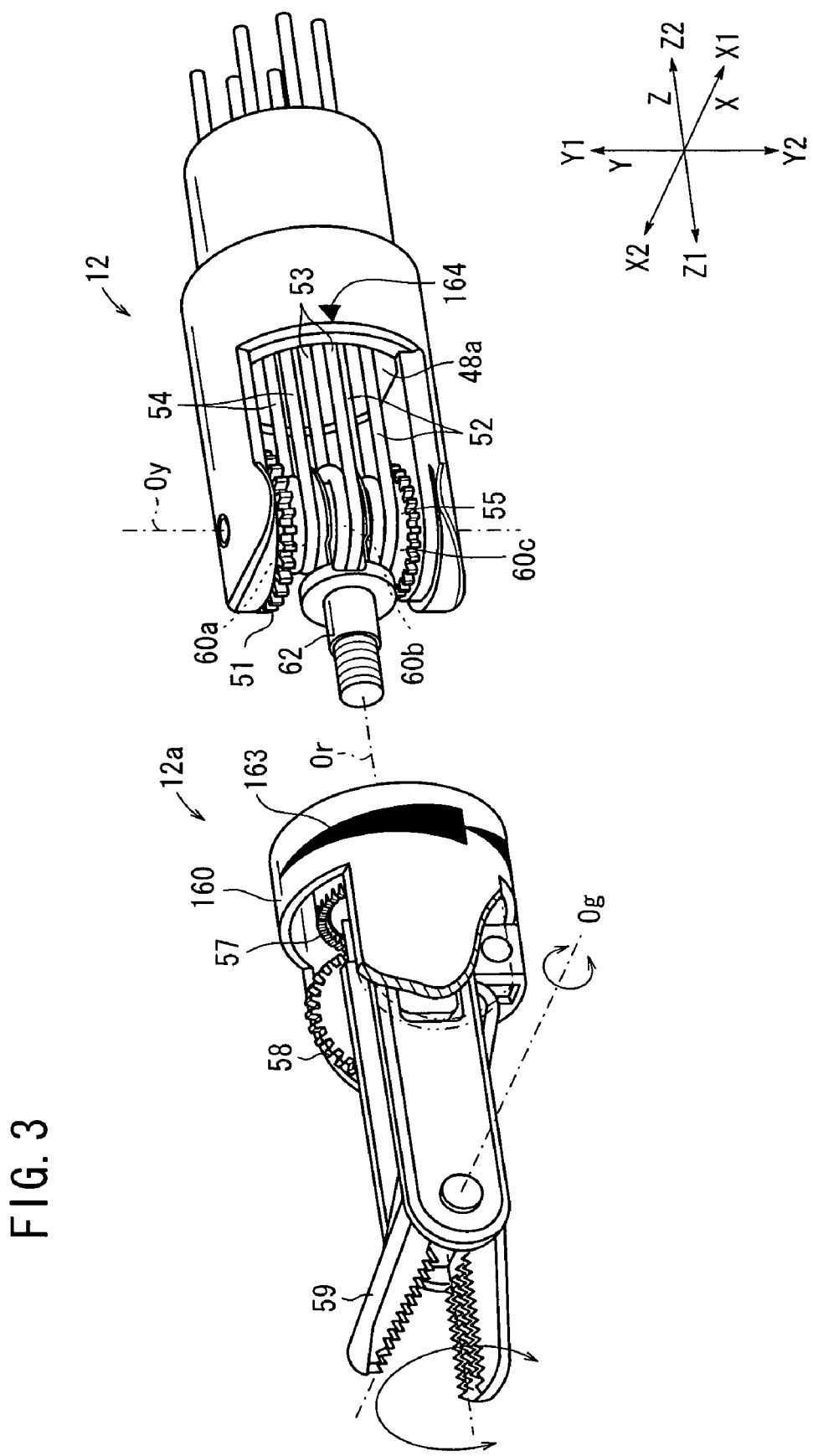
FIG. 3 is an exploded perspective view of a working unit of the manipulator.

As shown in FIG. 3, the working unit 12 incorporates therein mechanisms providing three degrees of freedom. These mechanisms include a mechanism (tilting mechanism, pivot shaft) having a first degree of freedom for angularly moving a distal end portion 12a that is positioned ahead of a first rotational axis Oy extending along the Y-axis direction in yawing directions about the first rotational axis Oy, a mechanism (rolling mechanism) having a second degree of freedom for angularly moving the distal end portion 12a in rolling directions about a second rotational axis Or extending along the Z-axis direction; and a mechanism for opening and closing the gripper 59 (opening and closing mechanism) about a third rotational axis Og extending along the X-axis direction.

The mechanism having the first degree of freedom can angularly move the distal end portion 12a in yawing directions through ±90° (a total of 180°), for example, and the mechanism having the second degree of freedom can angularly move the distal end portion 12a in rolling directions through ±180° (a total of 360°), for example.

The first rotational axis Oy of the yawing mechanism having the first degree of freedom may extend non-parallel to an axis C (see FIG. 5) of the connector 16, which extends from the proximal end to the distal end of the connector 16. The second rotational axis Or of the rolling mechanism having the second degree of freedom may extend along an axis of the working unit 12 at the tip end, i.e., at the gripper 59 thereof, so that the gripper 59 can roll around the second rotational axis Or.

The working unit 12 is actuated by the wires 52, 53, 54 that are trained around respective tubes 60a, 60b, 60c disposed in the working unit 12.

When the wires 52, 54 are actuated by the respective motors 40, 44, a gear 55 in the working unit 12 is rotated to rotate a face gear, not shown, in mesh therewith, thereby turning the distal end portion 12a in rolling directions. When the wire 54 is actuated by the motor 44, a gear 51 in the working unit 12 is rotated to rotate a face gear 57 in mesh therewith, and a gear 58 in mesh with the face gear 57, thereby opening or closing the gripper 59. When the wires 52, 53, 54 are actuated by the respective motors 40, 42, 44, a main shaft 62 in the working unit 12 is angularly moved to turn the gripper 59 in yawing directions.

The gripper 59 is supported inside a cylindrical case 160 having an outer circumferential surface coated with a mark 163 thereon, which gives a rough indication as to the angle through which the gripper 59 has turned in the rolling direction. The mark 163 comprises a plurality of triangles (e.g., three disposed at 120° intervals) having different triangular shapes (or different positions, colors, patterns, or three-dimensional shapes), for example, wherein the mark 163 extends fully around the outer circumferential surface. The user can confirm the angle through which the gripper 59 has rolled by visually checking the shape and relative position of the mark 163 on an endoscopic image. The working unit 12 also includes an indicator 164 on a proximal end thereof, which does not roll, for enabling the relative position of the mark 163 to be recognized. The user is thus able to recognize the angle through which the gripper 59 has rolled based on the relative position of the mark 163 with respect to the indicator 164.

Figure 4:
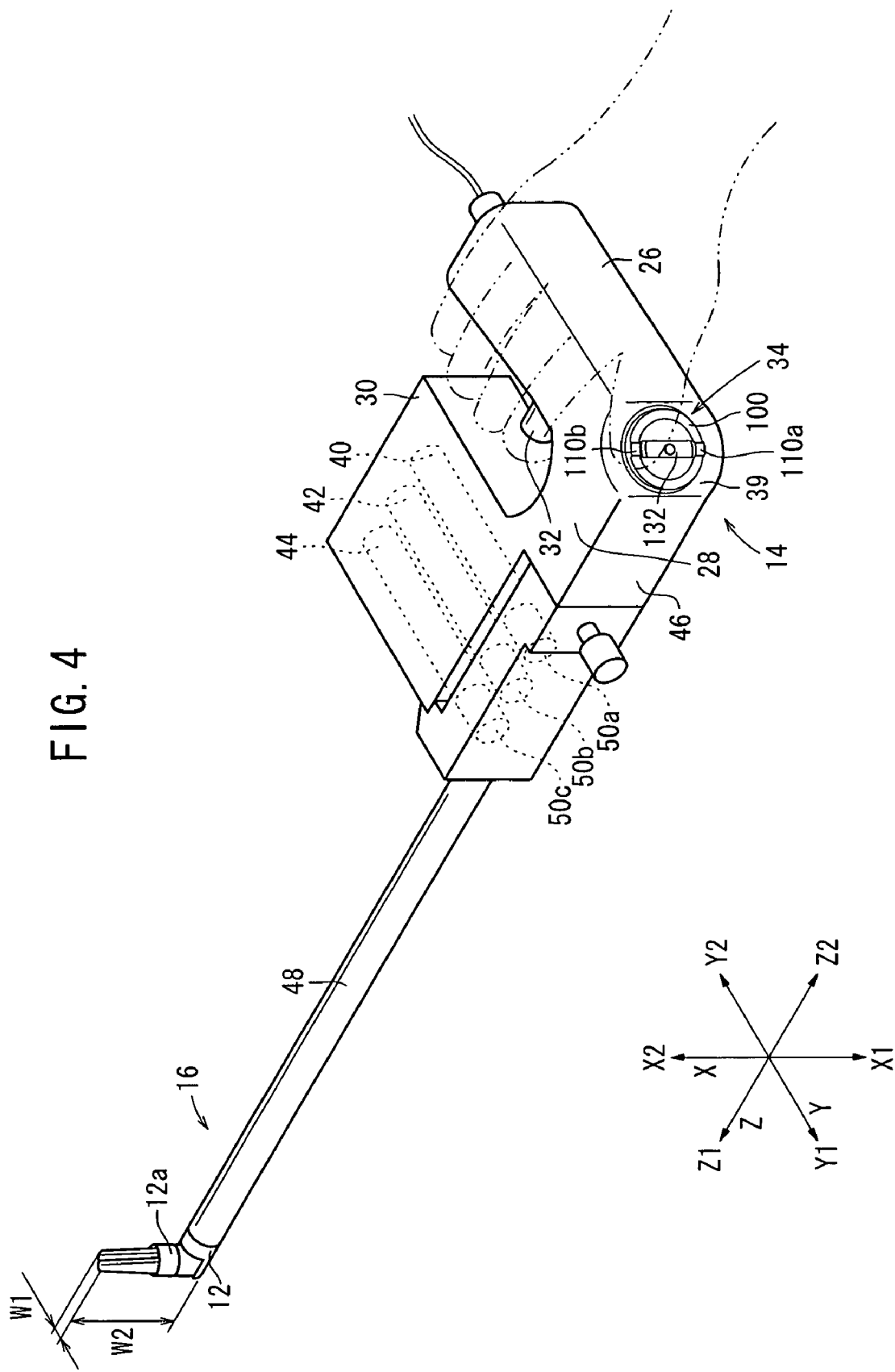
FIG. 4 is a perspective view of the manipulator when the manipulator is tilted by 90°.

The working unit 12 does not incorporate therein any mechanism having a degree of freedom for moving the working unit 12 in pitching directions, i.e., vertical directions. However, when the grip handle 26 is oriented horizontally, so as to tilt the manipulator 10 as a whole through 90°, as shown in FIG. 4, the movement of the working unit 12 in the yawing direction is converted into movement thereof in a pitching direction. Consequently, the lack of such a pitching mechanism does not pose any practical problem. As can be seen from FIG. 4, the distal end portion 12a has a width W1, which is equal to or smaller than the width of the connector shaft 48, and hence the distal end portion 12a can be inserted into narrow regions. Even when the distal end portion 12a is tilted, the height W2 thereof is small enough to permit the working unit 12 to be inserted into small regions and to perform surgical techniques therein. The shuttle ring 100 serves as an input means for applying a rolling command to the working unit 12. When the shuttle ring 100 is manually turned a greater angular interval, the working unit 12 is angularly moved in the rolling direction at a greater angular speed. When the shuttle ring 100 is not turned, the working unit 12 is held at rest in the rolling direction.

Figure 5:
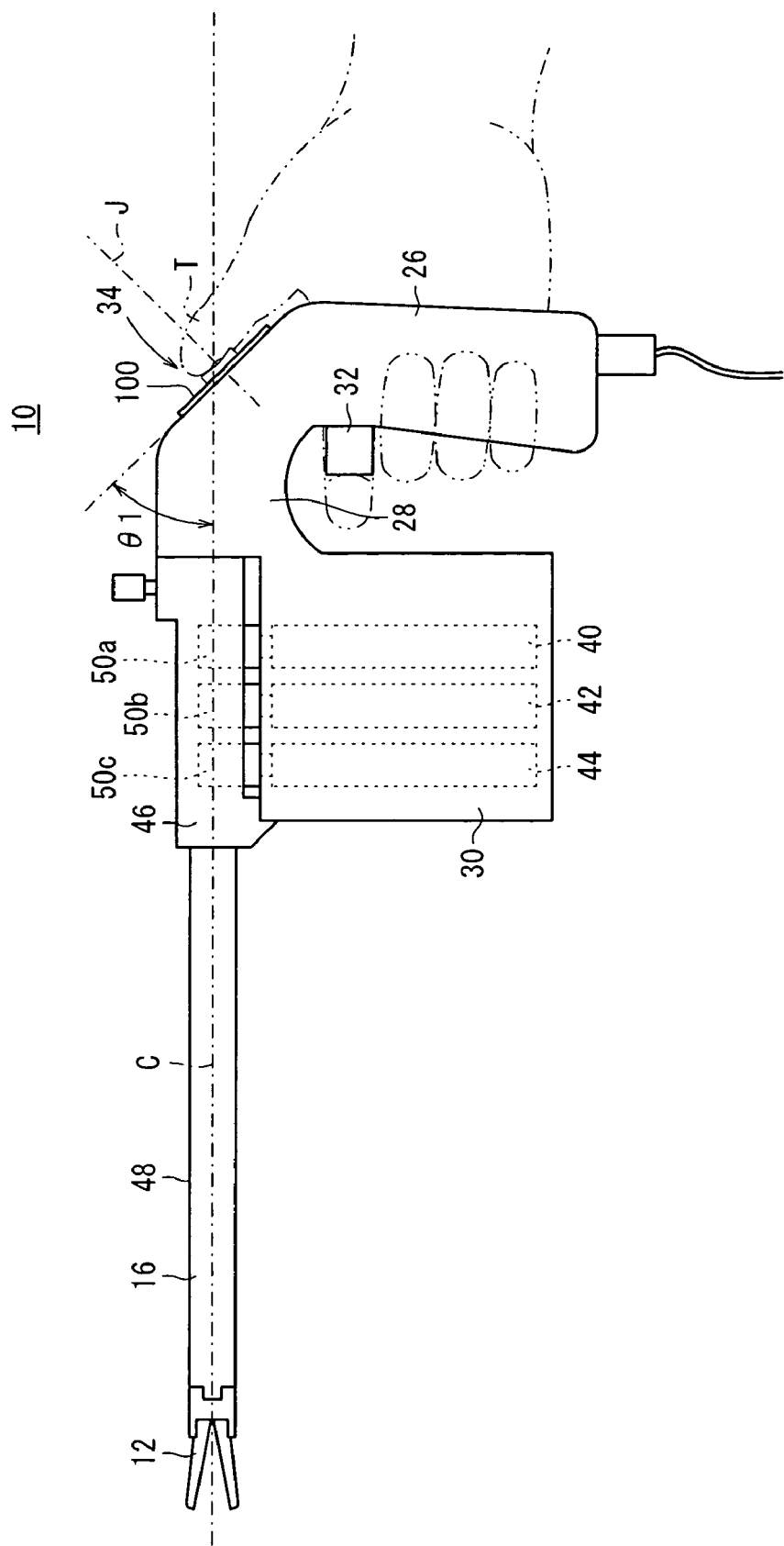
FIG. 5 is a side elevational view of the manipulator.

The shuttle ring 100 includes a pair of knobs (finger holders) 110a, 110b thereon, disposed in diametrically symmetric positions on the side face of the shuttle ring 100, which faces outwardly along the direction of an axis J thereof (see FIG. 5).

The shuttle ring 100 also includes a pad 132 having an end face 133 facing outwardly along the direction of the axis J. The end face 133 is slightly dented centrally and gradually slanted laterally. Specifically, the end face 133 has a low central flat surface 135, and left and right slanted surfaces 133a, 133b disposed one on each side of the low central flat surface 135. The flat and slanted surfaces 135, 133a, 133b can easily be distinguished from each other by tactile sensation. As shown in FIG. 5, the angle θ1 formed between the axis C of the connector shaft 48 and the plane in which the shuttle ring 100 rotates, i.e., the surfaces of the composite input unit 34 and the flat area 39, is set at 45°. The angle θ1 may lie within a range of from 35° to 55°, so that the shuttle ring 100 matches the natural position and the movable range of the thumb.

Since the width W1 and height W2 of the distal end portion 12a are sufficiently small, the distal end portion 12a can easily be inserted into a small space 250 (see FIGS. 12 through 20). Previously, it has been very difficult for conventional forceps having small degrees of freedom to adjust the direction of the gripper 59 and to enable the gripper 59 to be inserted into small spaces.

Figure 6:
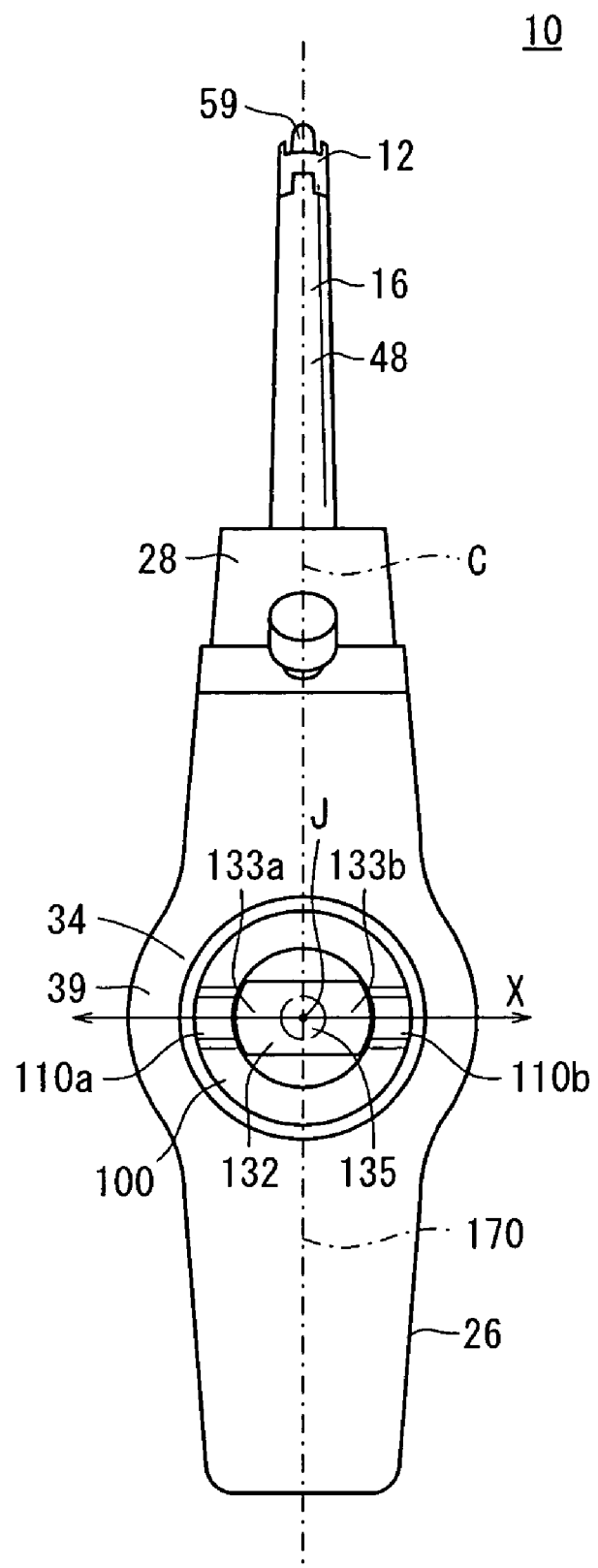
FIG. 6 is a plan view of the manipulator as seen along the rotational axis of a shuttle ring.

As shown in FIG. 6, the shuttle ring 100 has a horizontally central line 170 aligned with the longitudinal axis C of the connector shaft 48, as viewed along the rotational axis J of the shuttle ring 100. Consequently, the user is able to feel that the rolling mechanism of the working unit 12 operates concentrically, with the shuttle ring 100 in direct relationship thereto, and therefore the manipulator 10 is easy to operate.

Furthermore, since it is horizontally symmetrical in shape, the manipulator 10 can be used by either the right hand or the left hand. In FIG. 6, the manipulator 10 is illustrated in perspective to facilitate understanding of the way in which the manipulator 10 is seen from the viewpoint of the user.

Figure 7:
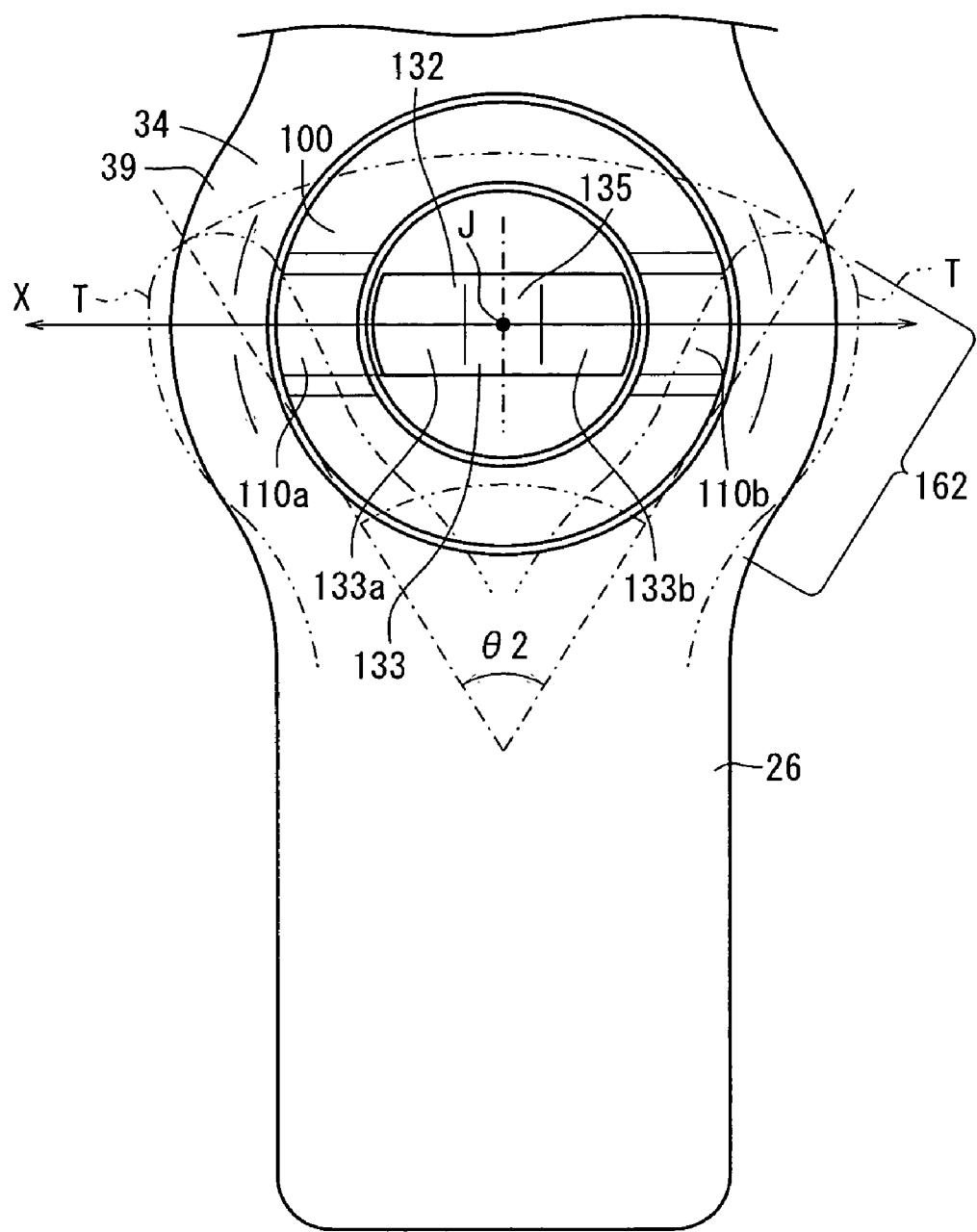
FIG. 7 is a view showing a surface region of a composite input unit.

As shown in FIG. 7, the pad 132 and the shuttle ring 100 of the composite input unit 34 are coaxially disposed around the axis J in a concentrated and compact configuration.

When the user applies the thumb to either one of the knobs 110a, 110b and pushes the knob up to turn the shuttle ring 100 in one direction, the working unit 12 is turned (i.e., rolled) in the same direction. Therefore, the rolling mechanism of the working unit 12 and the shuttle ring 100 turn in the same direction, so that the user is able to operate the working unit 12 easily and intuitively. Furthermore, the single shuttle ring 100 allows the rolling mechanism to turn in opposite directions. Therefore, the shuttle ring 100 does not require an increased number of input members, and the shuttle ring 100 is simple in structure and easy to operate.

Since the shuttle ring 100 has an annular shape, the shuttle ring 100 is easily visually recognized as an input means for entering rolling commands. Therefore, the user can easily learn and will not quickly forget how to use the shuttle ring 100. However, the operation command unit 14 can be designed to incorporate other input means for entering rolling commands. For example, the operation command unit 14 may have an input means that can be turned arcuately or moved angularly around the axis J, with only the knobs 110a, 110b being exposed on the surface, or having a C-shaped ring that is partially open.

Although the shuttle ring 100 and the pad 132 are disposed in a concentrated fashion, since they are separated mechanically from each other, the user can easily operate both the shuttle ring 100 and the pad 132 separately from each other, without becoming confused concerning usage thereof.

The pad 132 is located inside of the shuttle ring 100, and hence the pad 132 is compact and can be operated by moving the thumb within a small range. A single pad 132 allows the yawing mechanism to turn in opposite yawing directions. Therefore, the pad 132 does not require an increased number of input members, and the pad 132 is simple in structure and easy to operate.

The knobs 110a, 110b and the pad 132 are juxtaposed in the X direction and disposed within the shuttle ring 100, which has an appropriate diameter for this purpose. The knobs 110a, 110b and the pad 132 are thus positioned within a movable range of the finger pad T of the thumb, and therefore can be operated highly effectively.

Specifically, when the user grips the grip handle 26, the finger pad T of the thumb is naturally placed near the central flat surface 135 of the pad 132. If the thumb is movable within a general range defined by an angle θ2, which is achieved when the second joint (central joint) of the thumb and the third joint (proximal joint) of the thumb are moved, then the knobs 110a, 110b and the pad 132 are positioned within an arcuate range 162 inside of which the finger pad T moves. Accordingly, the knobs 110a, 110b and the pad 132 can be operated in a concentrated fashion by the thumb, without causing undue motions of the thumb.

The surface of the composite input unit 34 lies substantially flush with the flat area 39, with the exception that only the knobs 110a, 110b slightly project from the surface of the composite input unit 34. Therefore, when the user moves the finger pad T in the X direction, the user need only move the finger pad T along the substantially flat surface of the composite input unit 34. Therefore, the user can operate the composite input unit 34 with ease.

For performing techniques during surgical operations using the manipulator 10, the user operates the composite input unit 34 as follows:

First, the user applies the finger pad T of the thumb lightly to the central flat surface 135.

For moving the working unit 12 to the left in a yawing direction, the user moves the finger pad T from the central flat surface 135 onto the left slanted surface 133a and depresses the left slanted surface 133a. Since the left slanted surface 133a is apart from the central flat surface 135 and is positioned to the right of the knob 110a, the user finds it easy to confirm the position of the left slanted surface 133a through tactile sensation, without the need to look at the user's hand. For moving the working unit 12 to the right in a yawing direction, the user depresses the right slanted surface 133b, and thus can easily confirm the position of the right slanted surface 133b, basically in the same manner as with the position of the left slanted surface 133a.

For rolling the working unit 12, the user moves the finger pad T further to the left, until the finger pad T hits the knob 110a. The user then either pushes the knob 110a upwardly or pulls the knob 110a downwardly. When the user moves the finger pad T to the left along the surface of the composite input unit 34, the finger pad T touches the knob 110a naturally. Therefore, it is easy for the user to confirm the position of the knob 110a. Alternatively, the user may operate the knob 110b to roll the working unit 12. It also is easy for the user to confirm the position of the knob 110b, basically in the same manner as with the position of the knob 110a. Since the knobs 110a, 110b protrude appropriately from the surface of the composite input unit 34, the knobs 110a, 110b can easily be pushed upwardly or pulled downwardly with a light force.

When the user does not operate the composite input unit 34, the user may hold his or her thumb on the flat area 39. If the user wishes to move the working unit 12 in a rolling or a yawing direction with the thumb, which has been placed on the left end of the flat area 39, the user moves the finger pad T to the right along the flat area 39 and the composite input unit 34. Since the finger pad T naturally touches and comes into contact with the knob 110a, the left slanted surface 133a, the right slanted surface 133b, and the knob 110b in succession, the user can confirm the positions of such parts through tactile sensation, without the need for the user to look at the hand.

Because the knobs 110a, 110b and the pad 132 are located in adjacent positions, the working unit 12 can be both rolled and yawed in a composite motion with a single thumb. For example, if the working unit 12 is to be yawed to the left and rolled clockwise, then the user places the thumb both on the left slanted surface 133a and on the knob 110a, while depressing the left slanted surface 133a and pushing the knob 110a upwardly. If the working unit 12 is to be yawed to the right and rolled clockwise, the user places the thumb both on the right slanted surface 133b and on the knob 110b, while depressing the right slanted surface 133b and pulling the knob 110b downwardly.

The intracoelomic suturing and ligating method according to this embodiment of the present invention shall be described below with reference to the flowchart shown in FIG. 9. The intracoelomic suturing and ligating method is carried out using two manipulators 10, and may be applied, for example, to performing an endoscopic prostatectomy. One of the two manipulators 10 will be referred to as a manipulator 10a while the other is referred to as a manipulator 10b. Alternatively, the manipulator 10a and a laparoscopic forceps may be used when performing the intracoelomic suturing and ligating method.

Figure 8:
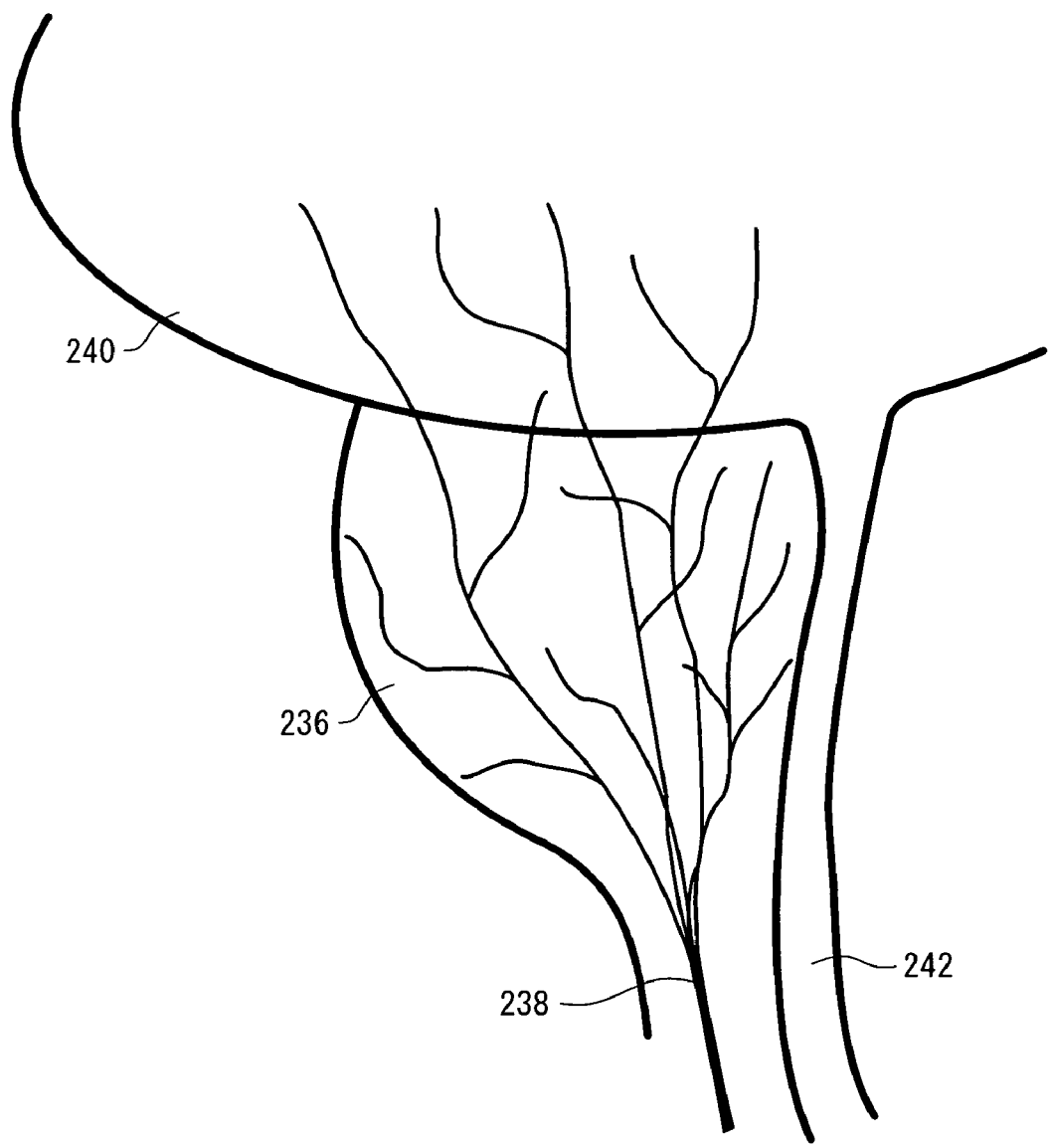
FIG. 8 is a view showing a DVC, a prostate gland, and a bladder.

As shown in FIG. 8, the prostate gland 236 and the bladder 240 are surrounded by veins, which have distal end portions put together and extending in parallel to the urinary duct 242. In FIG. 8, the upward direction represents the superior direction of the body, and the downward direction the inferior direction of the body, while the body is viewed from a lateral side thereof. For removing the prostate gland 236, it is first necessary to separate the urinary duct 242 from the prostate gland 236. To separate the urinary duct 242, the DVC 238 parallel to the urinary duct 242 must be ligated (DVC ligation) for arresting hemorrhage.

Figure 12:
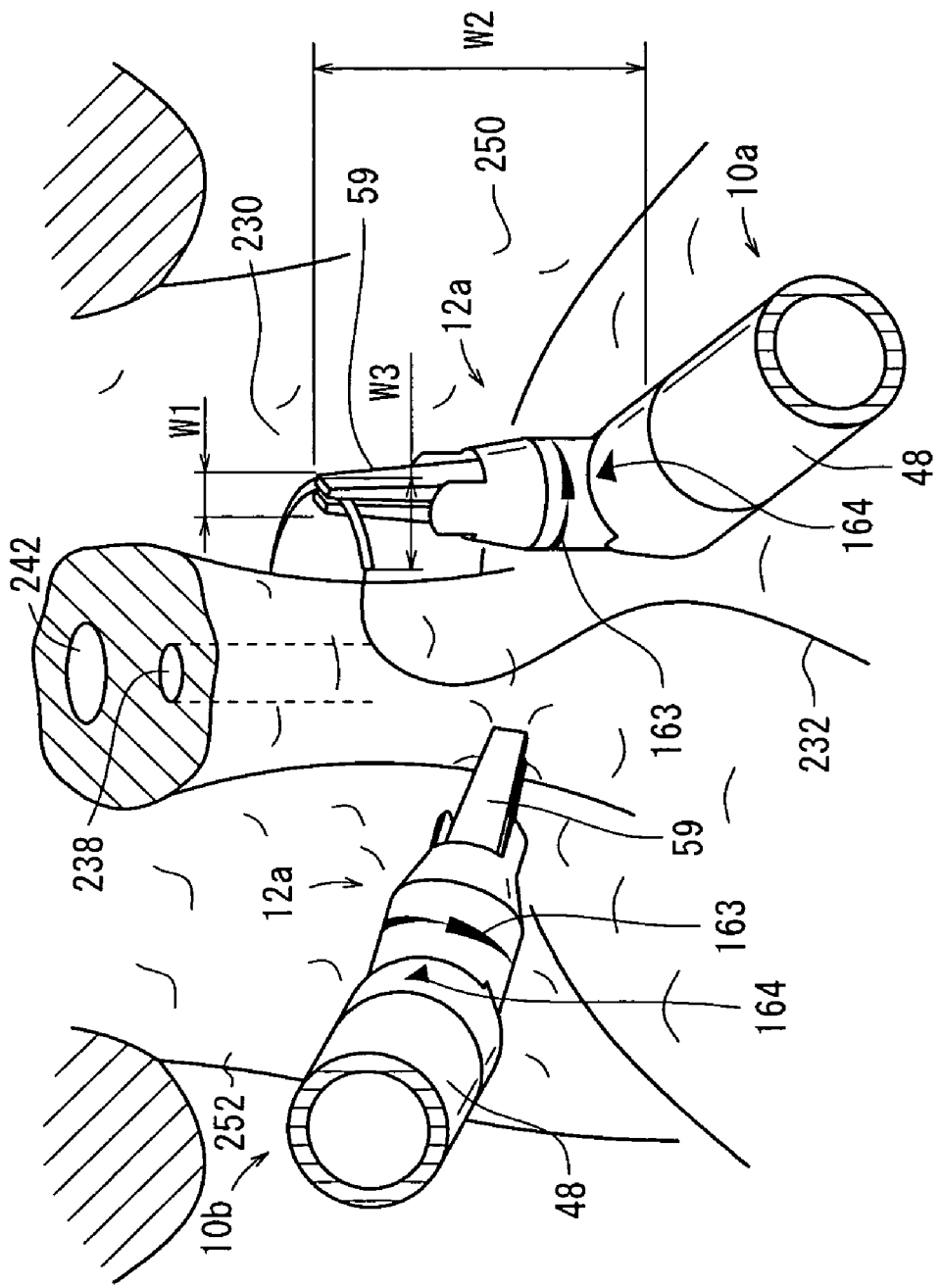
FIG. 12 is a view showing the manner in which the gripper, belonging to one of two manipulators, is inserted into a recess and positioned near the DVC while gripping the curved needle.

For ligating the DVC 238, it is necessary to place a curved needle 230 with a suture strand 232 connected thereto behind the DVC 238 inside of the small space or body cavity 250 (see FIG. 12). With conventional forceps, it is difficult to perform such a technique of placing the curved needle 230 behind the DVC 238. The curved needle 230 has an arcuate shape.

Figure 9:
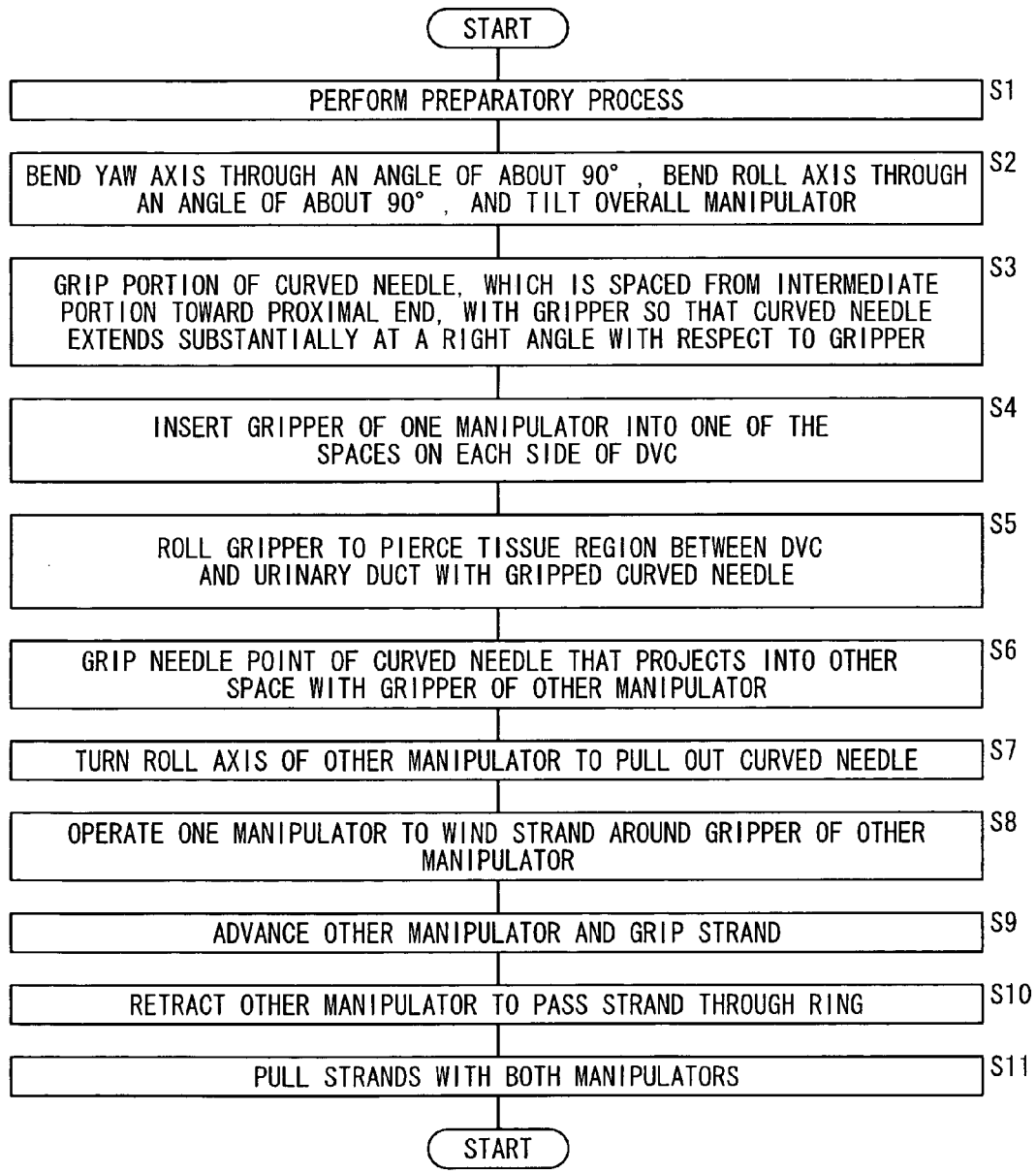
FIG. 9 is a flowchart of the intracoelomic suturing and ligating method according to the embodiment of the present invention.

In the intracoelomic suturing and ligating method according to the present embodiment, a preparatory process is performed in step S1, as shown in FIG. 9. The preparatory process includes inserting the manipulators 10a, 10b and an endoscope into the body cavity 250, introducing a gas into the body cavity, and peeling off tissues around the DVC 238.

Figure 10:
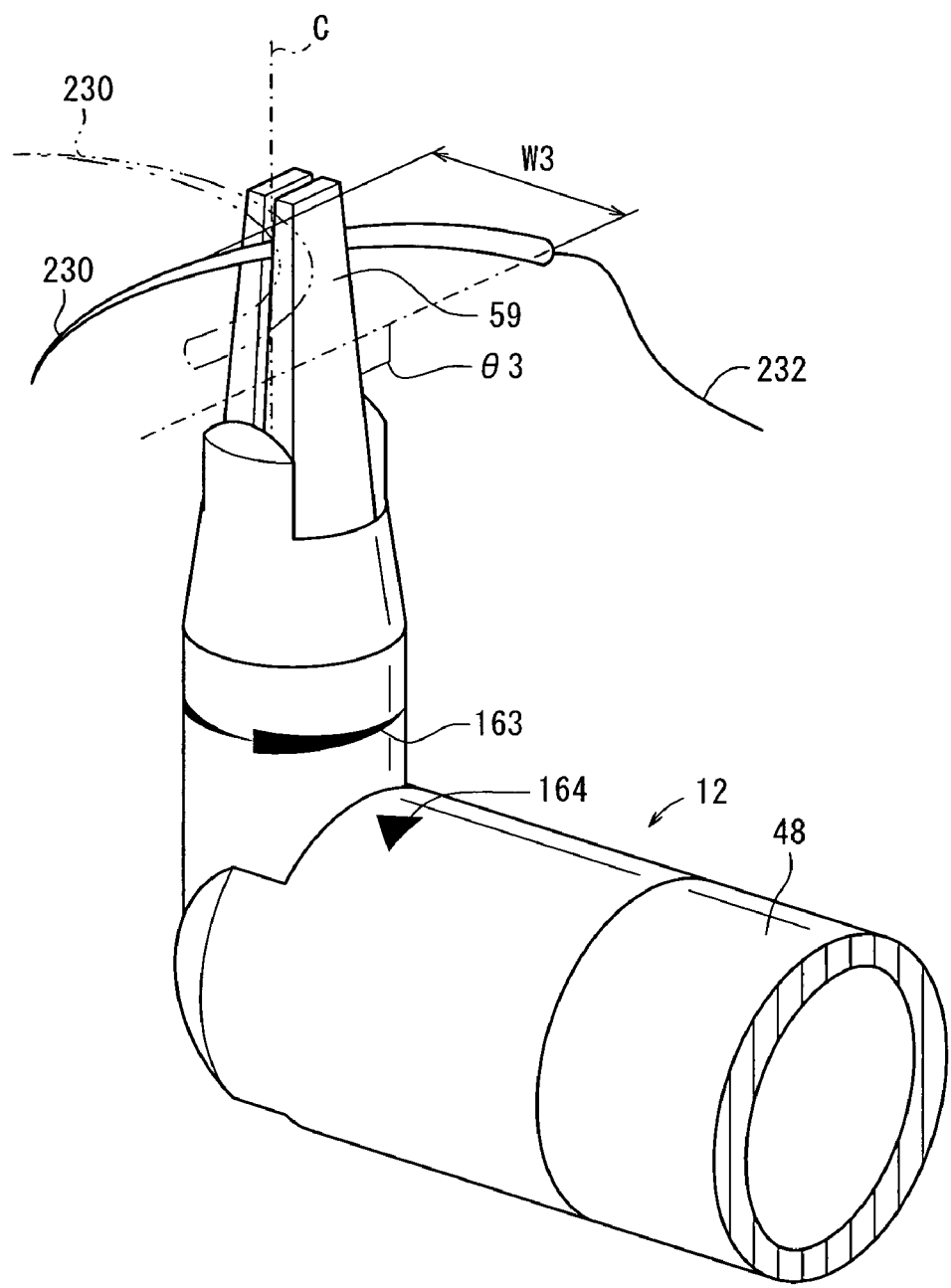
FIG. 10 is a perspective view of the working unit with a gripper portion thereof tilted by 90°.

In step S2, as shown in FIG. 10, the yaw axis (first rotational axis Oy) of the manipulator 10a is bent from its initial posture (0° position) through an angle of about 90°, and the roll axis (second rotational axis Or) of the manipulator 10a is bent from its initial posture (0° position) through an angle of about 90°. As shown in FIG. 4, the entire manipulator 10a may be tilted in order to orient the grip handle 26 horizontally and to adjust the orientation of the gripper 59. The yaw axis, the roll axis, and the manipulator 10a overall may be bent and tilted, either successively in any sequence or at the same time.

The yaw axis of the manipulator 10a is mechanically limited in angular movement, within a range of ±90°. The orientation of the gripper 59 can easily be set to one of the stroke ends of the ±90° range. Specifically, the user operates the pad 132 (see FIG. 7) for a relatively long period of time, until the gripper 59 becomes immovable, while confirming an endoscopic image thereof.

Figure 11:
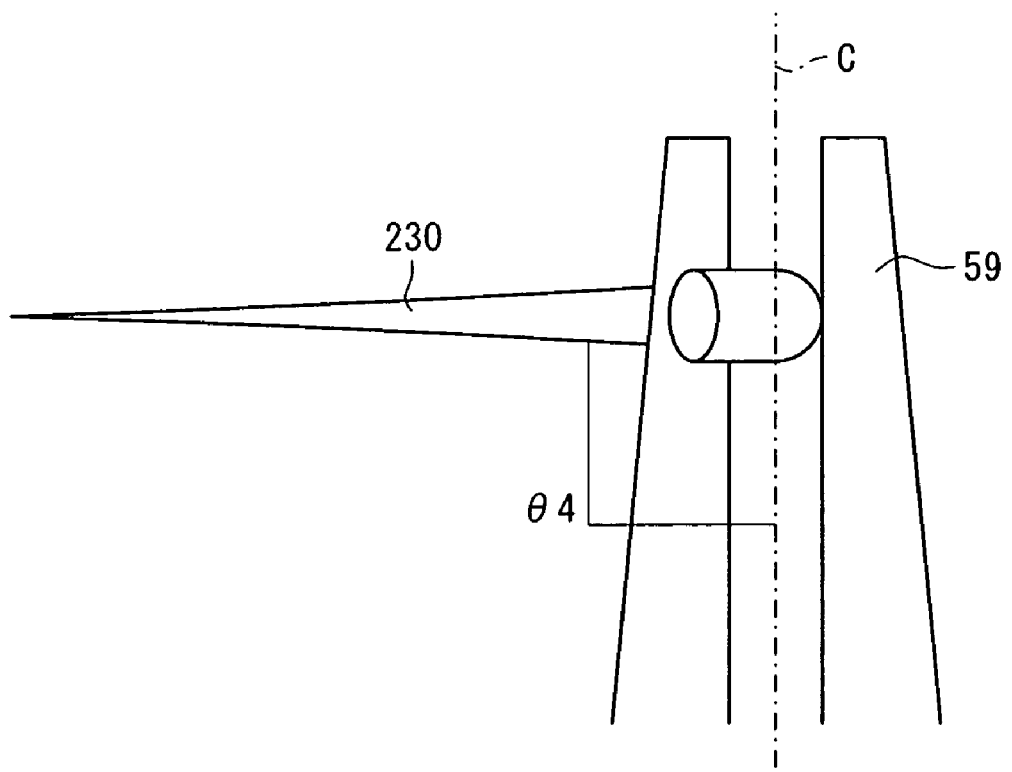
FIG. 11 is a side elevational view of the gripper, which grips a curved needle.

In step S3, as shown in FIG. 10, a portion of the curved needle 230, which is spaced slightly from an intermediate portion toward the proximal end portion thereof, is gripped by the gripper 59 such that the curved needle 230 extends substantially at a right angle to the gripper 59. Specifically, when the curved needle 230 is gripped by the gripper 59, the axis C of the gripper 59 and the proximal end (gripped portion) of the curved needle 230 form an angle θ3 of 90°. Further, as shown in FIG. 11, the axis C of the gripper 59 as viewed in side elevation, and the direction in which the curved needle 230 extends, form an angle θ4 of 90°.

At this time, as shown in FIG. 10, the point of the curved needle 130 is initially oriented toward the user (toward the flexible scope). Then, after the curved needle 230 has been firmly gripped by the gripper 59, the roll axis is turned to its initial posture (refer to the imaginary lines shown in FIG. 10).

As shown in FIG. 12, spaces 250, 252 are present, one on each side of the DVC 238. In step S4, the user inserts the gripper 59 into the space 250. The spaces 250, 252 are provided by peeling off tissue from around the DVC 238 in step S1. The spaces 250, 252 have narrow, deep shapes as shown in FIG. 12. In FIGS. 12, 13, and 15 through 20, the upward direction represents the inferior direction of the body, and the downward direction the superior direction of the body, while the body is viewed from the head side thereof.

The working unit 12 is positioned slightly on the right side of the DVC 238, and inserted into the space 250 such that the distal end portion 12a lies parallel to the DVC 238. Although the space 250 is narrow, since the yaw axis of the gripper 59 has been bent 90°, it is possible to easily insert the working unit 12 while keeping the distal end portion 12a substantially parallel to the DVC 238 by advancing the connector shaft 48 in its longitudinal direction. The width W3 of the curved needle 230 is so small that the curved needle 230 can be inserted into the space 250 without hitting the DVC 238 and other nearby tissues when the connector shaft 48 is inserted into the space 250.

While the gripper 59 grips the curved needle 230 near its proximal end, at an angle of about 90°, the point of the curved needle 230 is placed deeply inside the space 250, and is directed toward a tissue region between the DVC 238 and the urinary duct 242. In step S4, as shown in FIG. 12, the user can also operate the other manipulator 10b, so as to pinch and hold the DVC 238.

Figure 13:
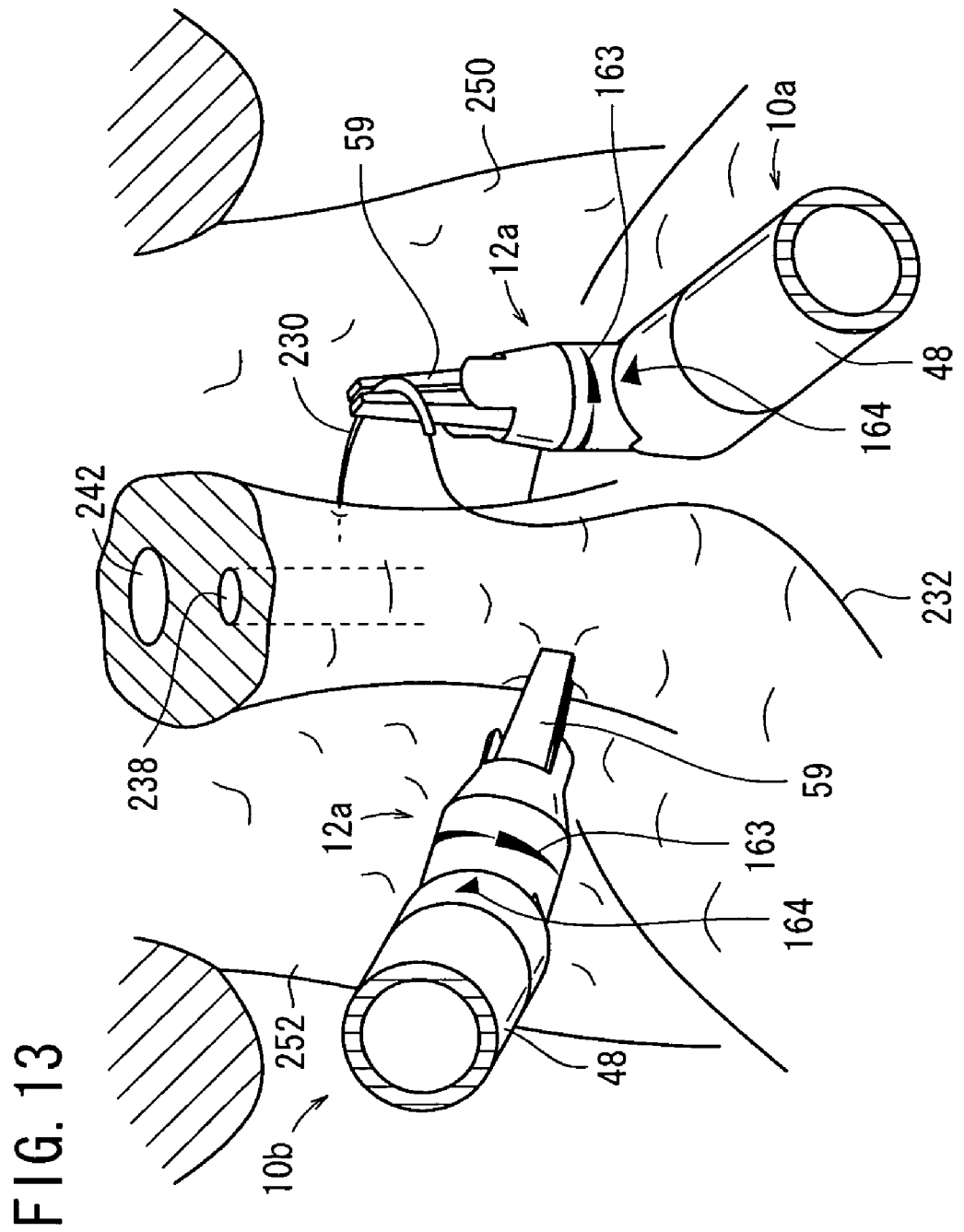
FIG. 13 is a view showing the manner in which the gripper is rolled about a roll axis thereof in order to cause the curved needle to pierce a living body.
Figure 14:
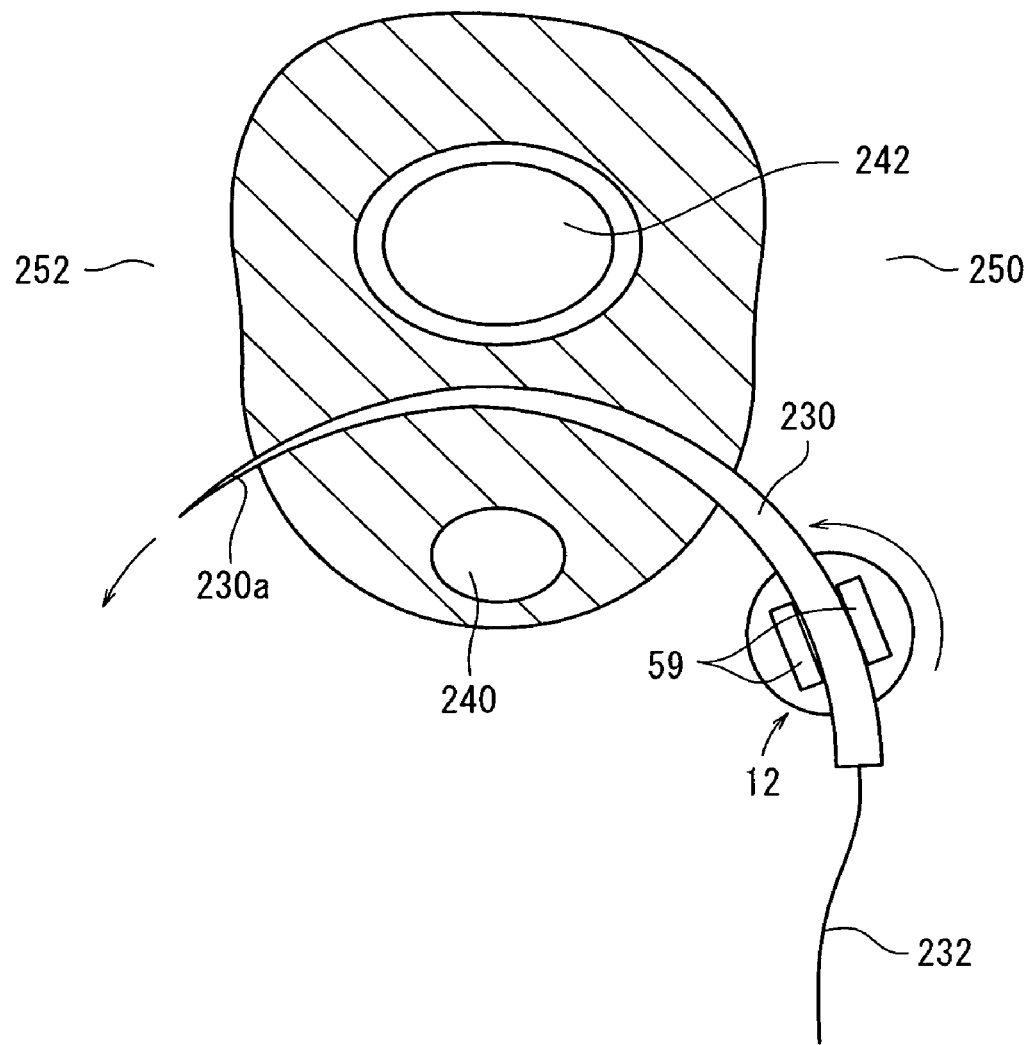
FIG. 14 is a view showing the manner in which the gripper is continuously rolled about the roll axis to cause the curved needle to penetrate the living body and to project into another recess.

In step S5, the user operates the shuttle ring 100 to roll the gripper 59, thereby causing the curved needle 230 to pierce the tissue region between the DVC 238 and the urinary duct 242, as shown in FIG. 13. When the user turns the gripper 59 through a sufficient angle, the point of the curved needle 230, denoted by 230a in FIG. 14, emerges from the tissue region and projects into the space 252. The curved needle 230 is thus moved by rolling the gripper 59 when the user pushes or pulls the knob 110a or 110b. During this time, the user may operate the shuttle ring 100, simply by moving the shuttle ring 100 a certain distance.

While the curved needle 230 pierces and moves through the tissue region between the DVC 238 and the urinary duct 242, the curved needle 230 applies a force that tends to pull the working unit 12, which is dragged, as it is not fixed in position. Accordingly, the curved needle 230 is not obstructed, but is allowed to move smoothly into and through the tissue region until the point 230a of the curved needle 230 projects into the space 252.

Without interrupting the motion of the curved needle 230, the user should then penetrate the tissue region all the way in one cycle with the curved needle 230. For moving the curved needle 230 from the space 250 to the space 252, it is necessary for the user to turn the roll axis of the gripper 59 through a considerable angle, e.g., an angle of 90° or more. Since the rotational axis of the gripper 59 has been turned through an angle of about 90° from the initial position, in a direction opposite to the direction in which the curved needle 230 pierces the tissue region, the gripper 59 can be turned through an angle of 90° or more, so that it is easy to push the curved needle 230 all the way through the tissue region into the space 252 in one operation.

The curved needle 230 can be moved from the space 250 to the space 252, primarily by rolling the gripper 59 in response to operation of the shuttle ring 100. Depending on circumstances of the patient and situations of the surgical operation, however, the gripper 59 may be yawed, the connector shaft 48 may be pushed in or pulled out, or the connector shaft 48 may be moved vertically and/or horizontally, at the same time that the gripper 59 is rolled.

Figure 15:
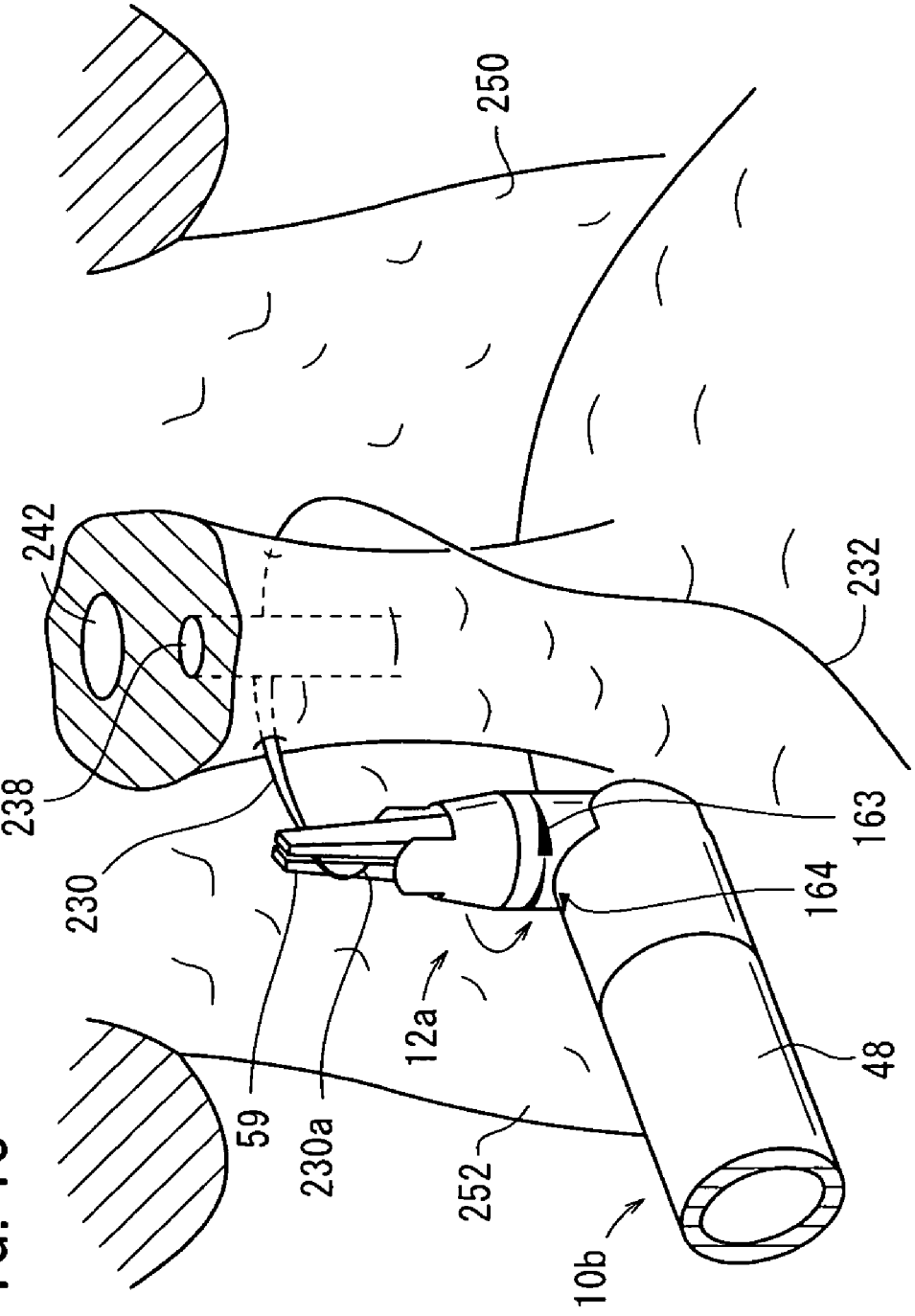
FIG. 15 is a view showing the manner in which the projecting end of the curved needle is gripped by another manipulator.

In step S6, as shown in FIG. 15, the needle point 230a, which has projected into the space 252, is gripped by the gripper 59 of the manipulator 10b. As with the manipulator 10a in step S2, the yaw axis of the manipulator 10b has been bent from an initial posture through an angle of about 90°, while the roll axis of the manipulator 10b has been bent from an initial posture through an angle of about 90°. Since the yaw axis has been bent through an angle of about 90°, the gripper 59 can easily grip the needle point 230a of the curved needle 230. At this time, the gripper 59 of the manipulator 10a is opened to release the proximal end of the curved needle 230.

Figure 16:
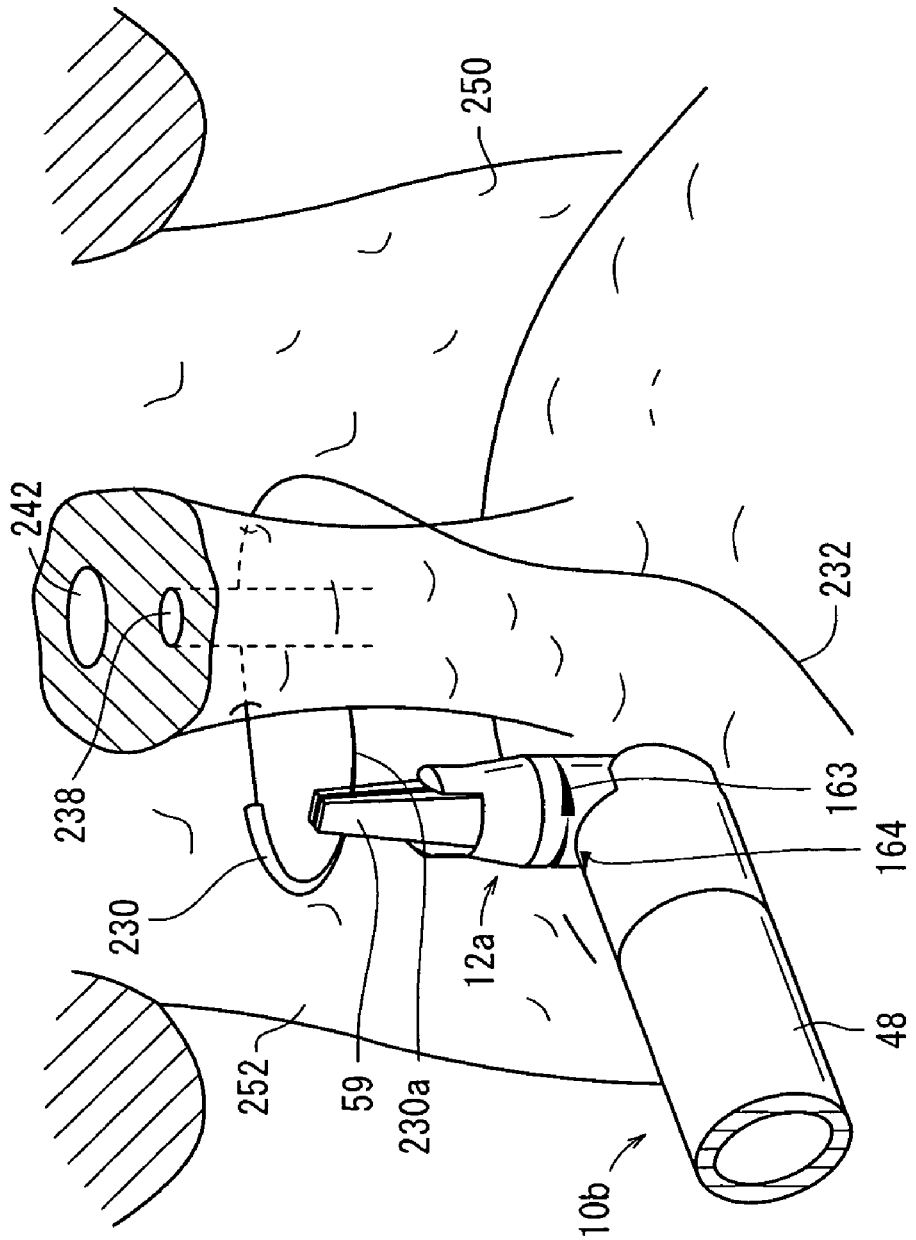
FIG. 16 is a view showing the manner in which the gripper of the other manipulator is rolled about a roll axis thereof to remove the curved needle from the living body.

In step S7, as shown in FIG. 16, the roll axis of the manipulator 10b is turned to pull the curved-needle 230 out of the tissue region. The user can easily pull out the curved needle 230 by pushing or pulling the knob 110a or 110b. For pulling out the curved needle 230, it is necessary for the user to turn the roll axis of the gripper 59 through a considerable angle, e.g., an angle of 90° or more. Since the rotational axis of the gripper 59 has been turned from its initial position, through an angle of about 90° in a direction opposite to the direction in which the curved needle 230 pierces the tissue region, the gripper 59 can be turned through an angle of 90° or more, thus making it easy to pull out the curved needle 230 in one operation.

Figure 17:
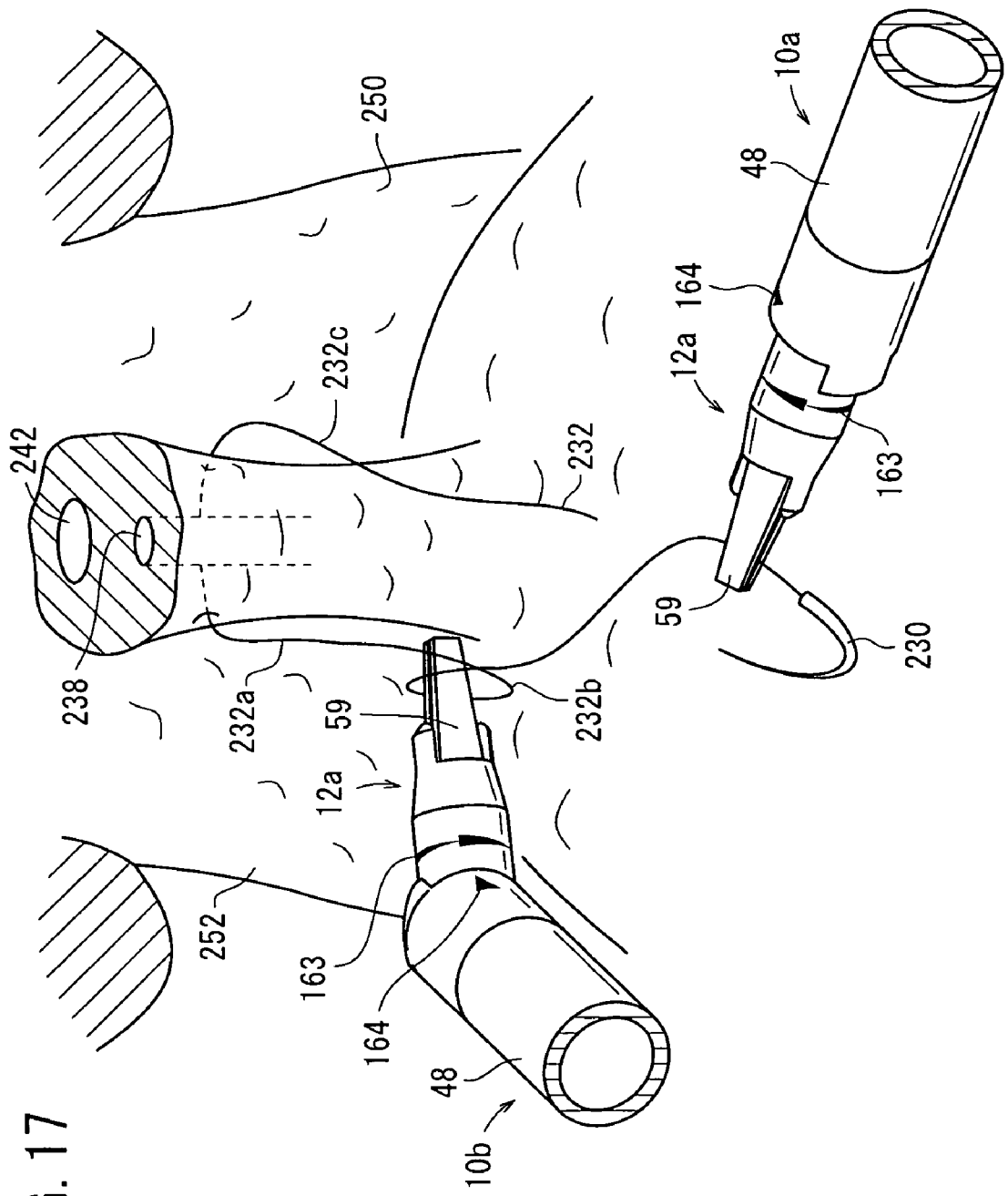
FIG. 17 is a view showing the manner in which one manipulator is operated to wind a suture strand around the gripper of the other manipulator.

In step S8, as shown in FIG. 17, the user operates the manipulator 10a to grip a suture strand 232a that is pulled into the space 252, while also operating the manipulator 10b to release the curved needle 230. At this time, the manipulator 10a is maintained in a righthand position, while the manipulator 10b is maintained in a lefthand position. Therefore, the manipulators 10a, 10b do not cross each other, and can easily be operated by the user.

The user operates the manipulator 10a to wind the suture strand 232a around the gripper 59 of the manipulator 10b, forming a ring 232b. The bent yaw axis of the gripper 59 of the manipulator 10b allows the suture strand 232a to be easily wound around the gripper 59. Thereafter, the gripper 59 of the manipulator 10b is rolled to bring a suture strand 232c remaining in the space 250 into an orientation so that the suture strand 232c can be easily gripped.

Figure 18:
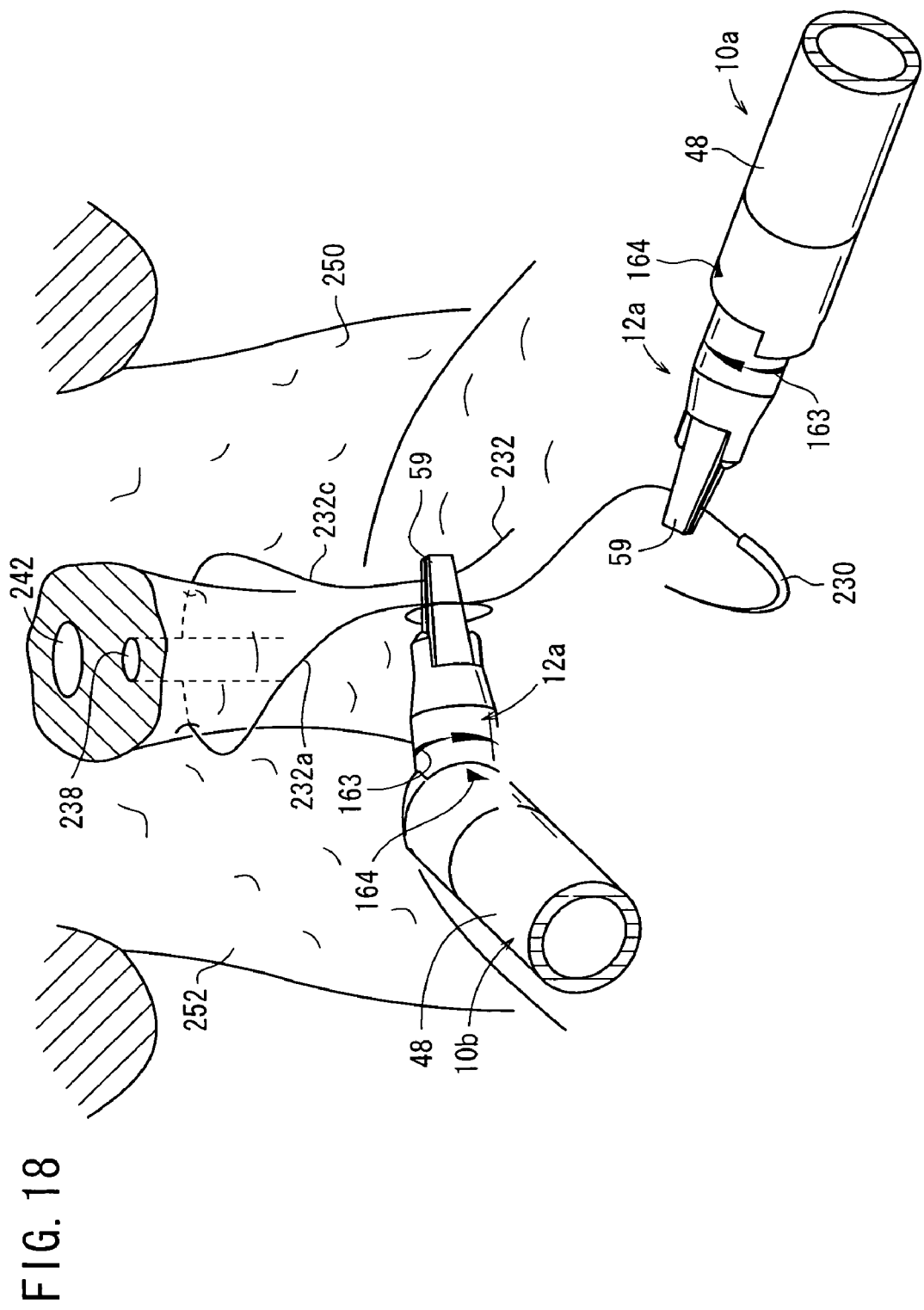
FIG. 18 is a view showing the manner in which the gripper of the other manipulator is advanced and grips the suture strand.

In step S9, as shown in FIG. 18, the distal end portion 12a of the manipulator 10b is advanced, and the gripper 59 thereof is operated to grip the suture strand 232c that remains within the space 250.

Figure 19:
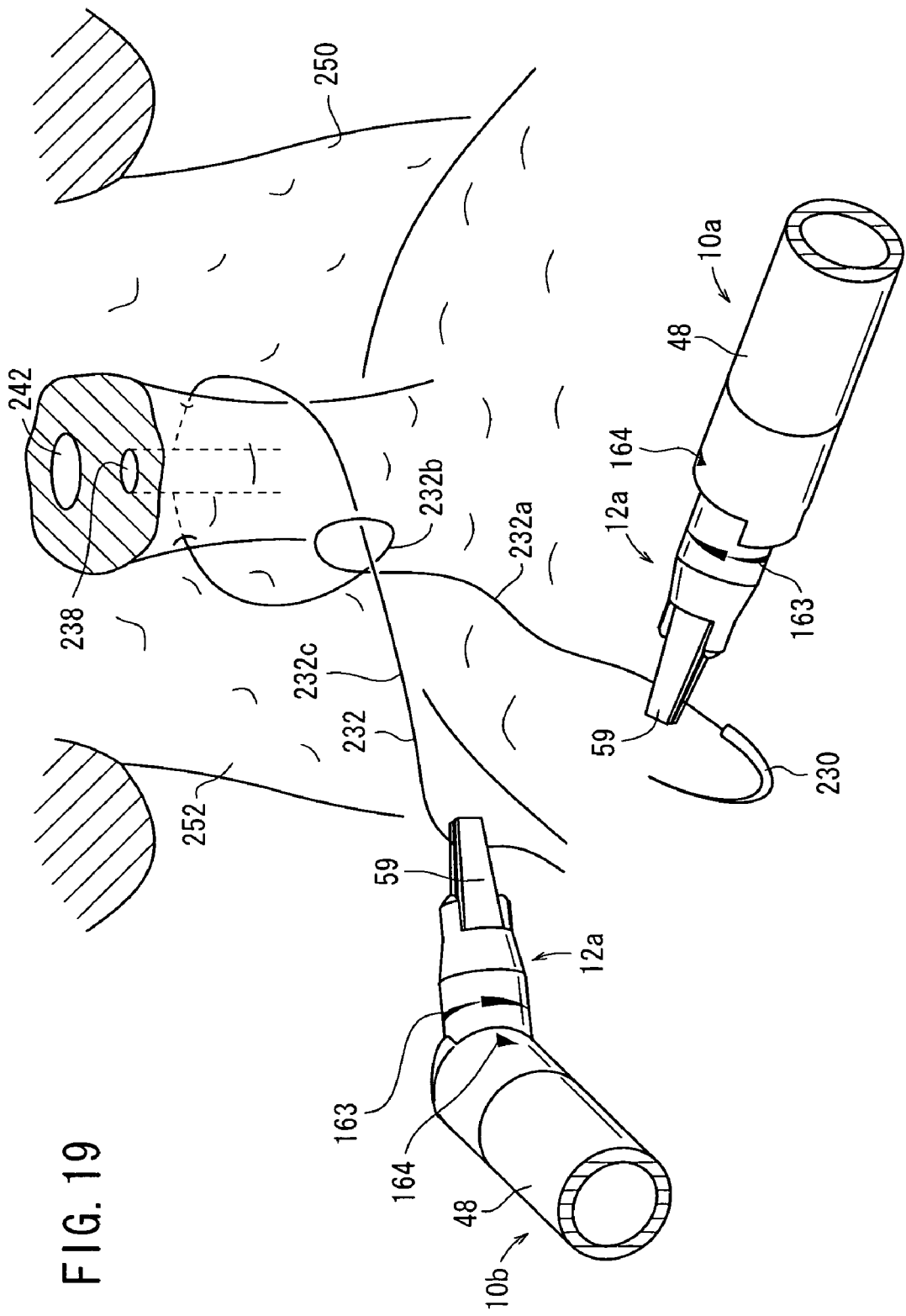
FIG. 19 is a view showing the manner in which the gripper of the other manipulator is retracted and pulls the suture strand through a ring of the other manipulator.

In step S10, as shown in FIG. 19, the user retracts the working unit 12 of the manipulator 10b out of the ring 232b, thereby pulling the suture strand 232c from the space 250 into and through the ring 232b.

Figure 20:
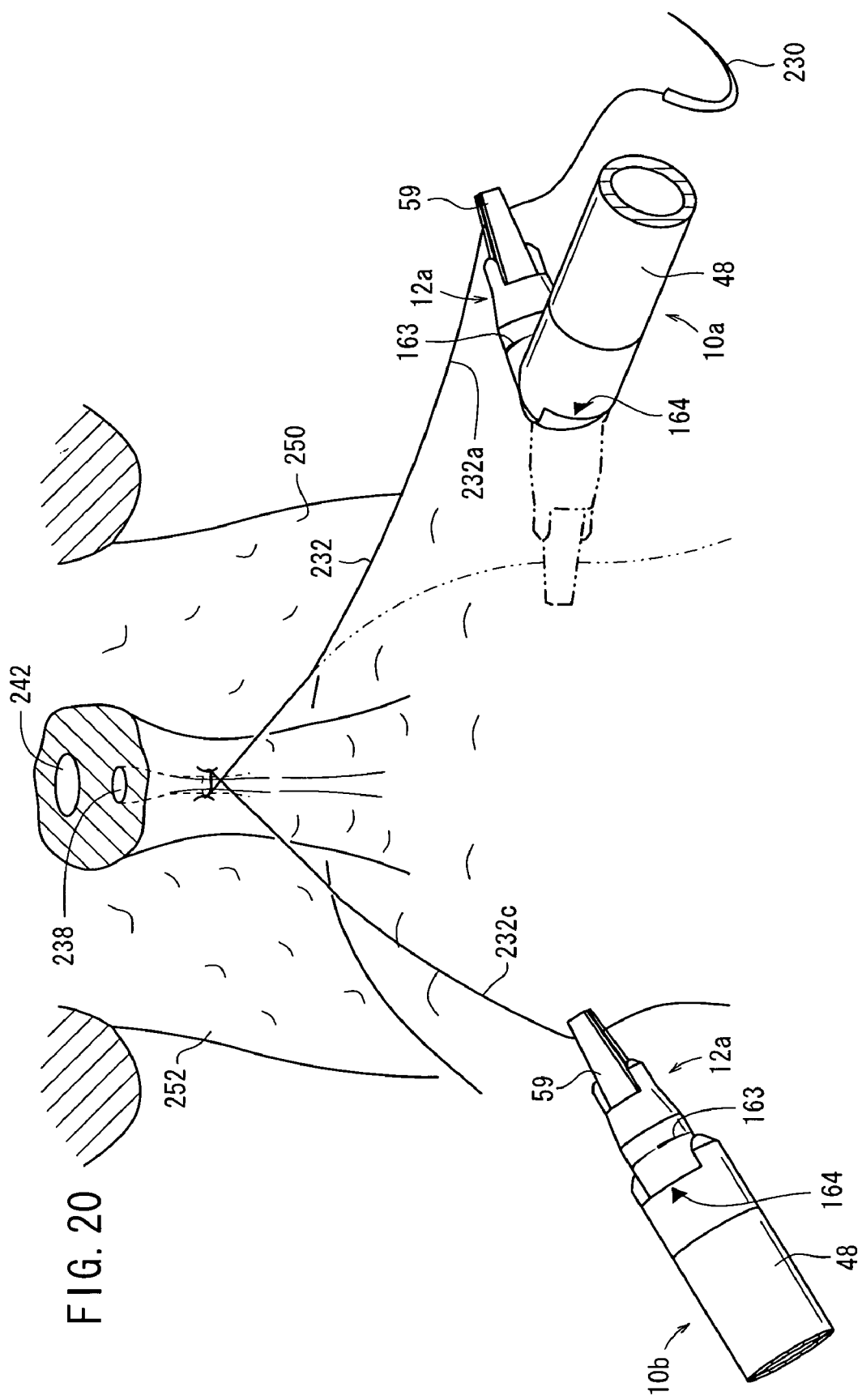
FIG. 20 is a view showing the manner in which a surgical knot is made on the DVC by the manipulators.

In step S11, as shown in FIG. 20, the user operates the manipulator 10a to pull the suture strand 232a, and also operates the manipulator 10b to pull the suture strand 232c, thereby contracting the ring 232b on the DVC 238 to ligate the DVC 238, for arresting hemorrhage.

At this time, if the user yaws at least one of the manipulators 10a, 10b to tilt the distal end portion 12a thereof, then the suture strands 232a, 232c can be pulled simply by operating the pads 132 (see FIG. 7), without any need for significantly moving the manipulators 10a, 10b in their entirety. In FIG. 20, the yaw axis of the distal end portion 12a of the manipulator 10a is shown as being moved from the imaginary-line position toward the solid-line position, so as to keep the suture strand 232a taut.

In this manner, a surgical knot is made on the DVC 238 by means of the suture strand 232. If necessary, a plurality of such surgical knots can be made by repeating the above process steps S2 through S11. Thereafter, any excessive length of the suture strand 232 may be cut off, whereupon the ligating process is now brought to an end.

Figure 21A:
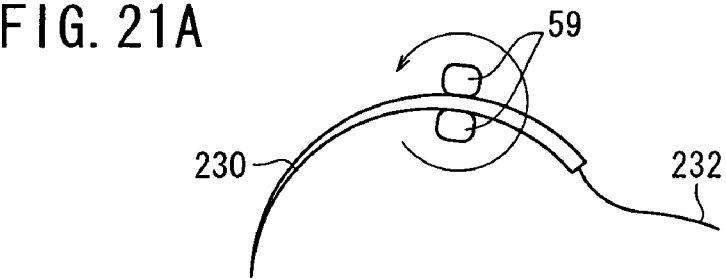
FIG. 21A is a view showing an initial phase of a needle turning process based on operation of a shuttle ring.
Figure 21B:
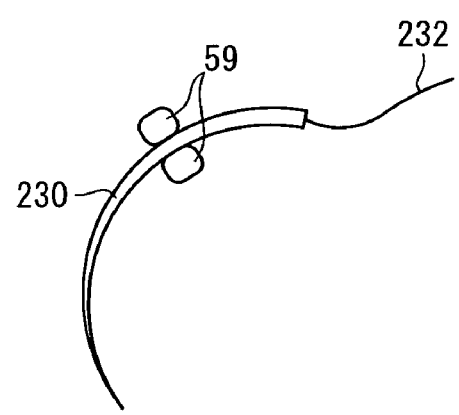
FIG. 21B is a view showing a middle phase of the needle turning process based on operation of the shuttle ring.
Figure 21C:
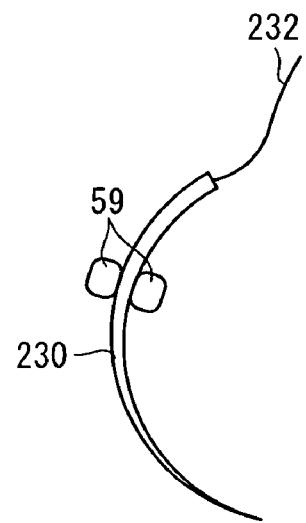
FIG. 21C is a view showing a final phase of the needle turning process based on operation of the shuttle ring.

As described above, the manipulator 10 includes a mechanism for angularly moving the gripper 59 of the working unit 12 about an axis along which the gripper 59 extends. The mechanism can be rolled in response to operation of the shuttle ring 100. Therefore, as shown in FIGS. 21A, 21B and 21C, regardless of the orientation of the main shaft 62 (see FIG. 3) about the first rotational axis Oy, the gripper 59 can easily be turned about its own axis, as viewed from the distal end thereof, in order to turn the curved needle 230. It is therefore easy to insert the curved needle 230 into the tissue region between the DVC 238 and the urinary duct 242, and to remove the curved needle 230 from the tissue region.

The intracoelomic suturing and ligating method according to the present invention is not limited to the aforementioned embodiment. It should be understood that various other configurations may be adopted without deviating from the scope of the invention as set forth in the appended claims.

What is claimed is:

1. An intracoelomic suturing and ligating method for use in performing a prostatectomy with a manipulator having an operating unit to be gripped by hand, a connector extending from the operating unit, and a working unit mounted on a distal end of the connector and including a rolling mechanism, a tilting mechanism, and an opening and closing mechanism, the method comprising the steps of:
   a) inserting said working unit into a body cavity in a living body;
   b) gripping a curved needle with said opening and closing mechanism;
   c) tilting said opening and closing mechanism with said tilting mechanism;
   d) placing said opening and closing mechanism near a dorsal vein complex (DVC) within said body cavity; and
   e) actuating said rolling mechanism to angularly move said opening and closing mechanism while keeping said opening and closing mechanism parallel with said DVC, so as to pierce said curved needle into body tissues of the living body around said DVC until a needle point of said curved needle projects from the body tissues,
   f) gripping said curved needle projecting from the body tissues with said opening and closing mechanism,
   g) actuating said rolling mechanism to angularly move said opening and closing mechanism while gripping said curved needle and keeping said opening and closing mechanism parallel with said DVC until said curved needle is pulled out from the body tissues,
   h) ligating said DVC after said curved needle is removed from the body tissues.

2. An intracoelomic suturing and ligating method according to claim 1, wherein said manipulator has an input unit comprising two finger holders disposed one on each side of a central line passing through a rotational axis thereof, for operating said rolling mechanism in response to turning movements thereof.

3. An intracoelomic suturing and ligating method according to claim 1, wherein said step c) comprises tilting said opening and closing mechanism through an angle of about 90° from the center of an operating range thereof, with said tilting mechanism.

4. An intracoelomic suturing and ligating method according to claim 1, wherein said step e) comprises angularly moving said opening and closing mechanism through an angle of about 90° from the center of an operating range thereof, with said rolling mechanism.

5. An intracoelomic suturing and ligating method according to claim 1, wherein said manipulator is a first manipulator, and the curved needle is gripped by said opening and closing mechanism of the first manipulator in step b), said steps a) through e) are carried out by the first manipulator, and said steps f) and g) are carried out by a second manipulator.

6. An intracoelomic suturing and ligating method according to claim 5, further comprising the step of:
   i) after said step e) and before said step f), tilting said opening and closing mechanism through an angle of about 90° from the center of an operating range thereof, with said tilting mechanism of the second manipulator.

7. An intracoelomic suturing and ligating method according to claim 5, further comprising the step of:
   j) after said step e) and before said step f), angularly moving said opening and closing mechanism through an angle of about 90° from the center of an operating range thereof, with said rolling mechanism of the second manipulator.

8. An intracoelomic suturing and ligating method according to claim 1, wherein said manipulator is a first manipulator, and the curved needle is gripped by said opening and closing mechanism of the first manipulator in step b), and further comprising a second manipulator, the step (h) further comprising after said curved needle is pulled out of the body tissues, tilting said opening and closing mechanism through an angle of about 90° from the center of an operating range thereof, with said tilting mechanism of the second manipulator, and moving a strand connected to said curved needle with said opening and closing mechanism of the first manipulator so as to wind the strand around said opening and closing mechanism of the second manipulator.

9. An intracoelomic suturing and ligating method according to claim 8, further comprising the step of:

k) operating the rolling mechanism of the second manipulator to set said opening and closing mechanism in an orientation for gripping a portion of said strand, which remains to be inserted into the body tissues.

10. An intracoelomic suturing and ligating method according to claim 1, the step (h) further comprising pulling said curved needle out of the body tissues, holding a strand connected to said curved needle with said opening and closing mechanism, and actuating said tilting mechanism to tilt said opening and closing mechanism, thereby pulling said strand when said DVC is ligated by said strand.

\* \* \* \* \*